US012582681B2

(12) United States Patent　　　(10) Patent No.:　US 12,582,681 B2

Rubio et al.　　　　　　　　　　　(45) Date of Patent:　　Mar. 24, 2026

(54) FERMENTED MILK PRODUCT FOR ADMINISTRATION IN CANIDS SUCH AS DOGS, AND USES THEREOF

(71) Applicant: AQUILON CYL S.L., León (ES)

(72) Inventors: Pedro Rubio, León (ES); Ana Carvajal, León (ES); Marta García, León (ES); Sandra González, León (ES)

(73) Assignee: AQUILON CYL S.L., León (ES)

( * ) Notice: Subject to any disclaimer, the term of this patent is extended or adjusted under 35 U.S.C. 154(b) by 766 days.

(21) Appl. No.: 17/642,602

(22) PCT Filed: Sep. 11, 2020

(86) PCT No.: PCT/EP2020/075480

§ 371 (c)(1),
(2) Date: Mar. 11, 2022

(87) PCT Pub. No.: WO2021/048362

PCT Pub. Date: Mar. 18, 2021

(65) Prior Publication Data

US 2023/0063695 A1　　　Mar. 2, 2023

(30) Foreign Application Priority Data

Sep. 13, 2019 　(EP) .................................... 19382794

(51) Int. Cl.
　　*A61K 35/744*　　　(2015.01)
　　*A61K 35/20*　　　(2006.01)
　　*A61P 1/00*　　　(2006.01)
(52) U.S. Cl.
　　CPC ............ *A61K 35/744* (2013.01); *A61K 35/20* (2013.01); *A61P 1/00* (2018.01)
(58) Field of Classification Search
　　None
　　See application file for complete search history.

(56) References Cited

FOREIGN PATENT DOCUMENTS

| | | |
|---|---|---|
| CN | 106 591 211 A | 4/2001 |
| EP | 1 625 795 A1 | 2/2006 |
| WO | 01/90311 A1 | 11/2001 |

OTHER PUBLICATIONS

Awaisheh et al., "Screening of Antibacterial Activity of Lactic Acid Bacteria Against Different Pathogens Found in Vacuum-Packaged Meat Products," *Foodborne Pathogens and Disease* 6(9):1125-1132, 2009.

Basra et al., "Fitness Tradeoffs of Antibiotic Resistance in Extraintestinal Pathogenic *Escherichia coli,*" *Genome Biol. Evol.*, 10(2):667-669, 2018.

Dortu et al., "Anti-listerial activity of bacteriocin-producing *Lactobacillus curvatus* CWBI-B28 and *Lactobacillus sakei* CWBI-B1365 on raw beef and poultry meat," *Letters in Applied Microbiology* 47:581-586, 2008.

EFSA, "Guidance on the assessment of bacterial susceptibility to antimicrobials of human and veterinary importance," *The EFSA Journal* 10(6):2740,1-10, 2012.

EFSA, "Guidance on the characterisation of microorganisms used as feed additives or as production organisms," *The EFSA Journal* 16(3):5206, Feb. 2018, (24 pages).

EFSA, "Opinion of the Scientific Panel on Additives and Products or Substances used in Animal Feed on a request from the Commission on micro-organism product "Reuteri Pig Powder" for use as feed additive in accordance with Council Directive 70/524/EEC," *The EFSA Journal* 229:1-7, 2005.

EFSA, "Update of the criteria used in the assessment of bacterial resistance to antibiotics of human or veterinary importance," *The EFSA Journal* 732:1-15, 2008.

Egervärn et al., "Transferability of a tetracycline resistance gene from probiotic *Lactobacillus reuteri* to bacteria in the gastrointestinal tract of humans," *Antonie van Leeuwenhoek* 97:189-200, 2010.

Hata et al., "Isolation and characterization of plantaricin ASM1: A new bacteriocin produced by *Lactobacillus plantarum* A-1," *International Journal of Food Microbiology* 137:94-99, 2009.

Kawai et al., "Structural and Functional Differences in Two Cyclic Bacteriocins with the Same Sequences Produced by Lactobacilli," *Applied and Environmental Microbiology* 70(5):2906-2911, May 2004.

Klare et al., "Evaluation of New Broth Media for Microdilution Antibiotic Susceptibility Testing of Lactobacilli, Pediococci, Lactococci, and Bifidobacteria," *Applied and Environmental Microbiology* 71:8982-8986, 2005.

Maynard et al., "Reciprocal Interactions of the Intestinal Microbiota and Immune System," *Nature* 489(7415):231-241, Sep. 2012.

Melnyk et al., "The fitness costs of antibiotic resistance mutations," *Evolutionary Applications* 8(3):273-283, 2015.

Monteagudo Mera, "Selección in vitro de microorganismos con potencial probiótico," Tesis doctoral, Universidad de León, 2010, (206 pages), (w/ English abstract).

Redfern et al., "Role of the gastrointestinal microbiota in small animal health and disease," *Veterinary Record* 181(14):1-7, 2017.

Rodríguez et al., "The composition of the gut microbiota throughout life, with an emphasis on early life," *Microbial Ecology in Health & Disease* 26:26050,1-17, 2015.

Schillinger et al., "Antibacterial Activity of *Lactobacillus sake* Isolated from Meat," *Applied and Environmental Microbiology* 55(8):1901-1906, Aug. 1989.

*Primary Examiner* — Oluwatosin A Ogunbiyi

(74) *Attorney, Agent, or Firm* — Seed Intellectual Property Law Group LLP

(57)　　　　　　　ABSTRACT

Fermented milk products can provide multiple benefits. However, it was commonly believed that fermented milk products are not suitable for the administration to canids as e.g. dogs can be intolerant to lactose. The present invention provides fermented milk products for administration to canids.

19 Claims, 6 Drawing Sheets

Figure 1

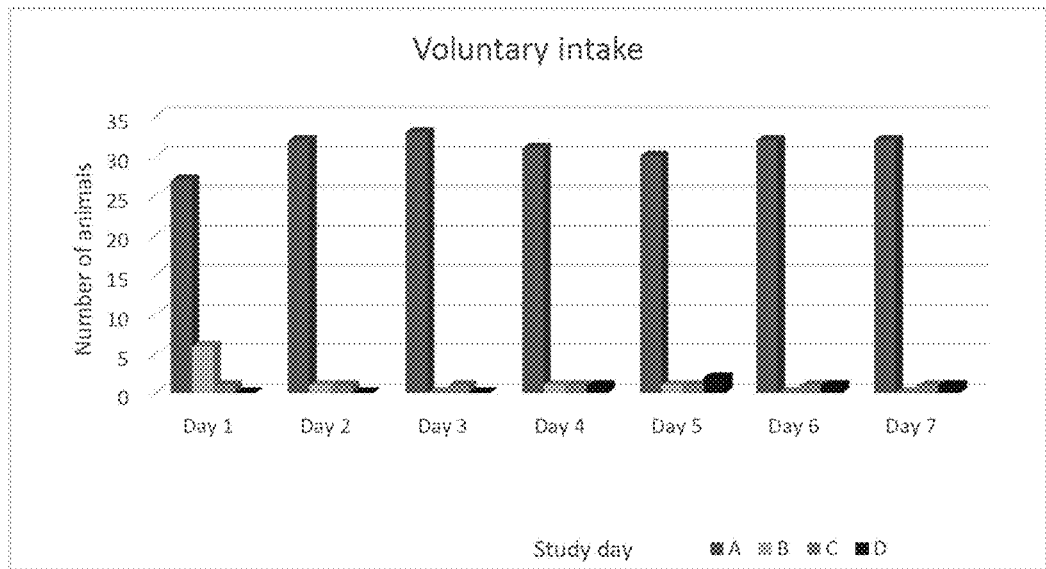

Evaluation of the animals' behaviour by each product offer for 7 consecutive days (A: Immediate intake, B: First explore and then eating, C: Smell and thereafter eating, D: Recognising but not eating). It can be seen that surprisingly, most dogs immediately ate the product at the beginning of the study, and the number of dogs that immediately ate the product surprisingly increased in the consecutive study days.

Figure 2

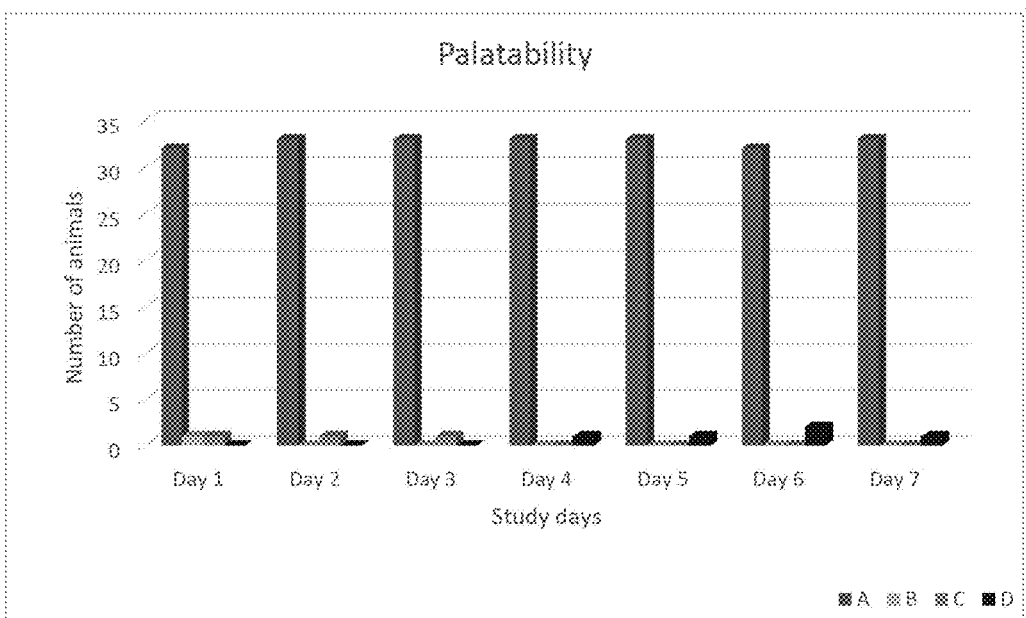

Evaluation of the product's intake for 7 consecutive days. A: Dogs ate all the product, B: Dogs started eating but did not finish, C: Dogs tasted but did not eat, D: Dogs smelled but did not taste. As can be seen, most dogs ate all offered product throughout the study.

Figure 3

| Ref. | Identification (Blast/ncbi) | %Sim. | Ref. | Identification (Blast/ncbi) | %Sim. |
|------|------------------------------|-------|------|------------------------------|-------|
| 1.1 | *Enterococcus faecalis* | >99 | 8.1 | *Enterococcus faecalis* | >99 |
| 2.1 | *Lactobacillus animalis* | >99 | 9.1 | *Enterococcus faecalis* | >99 |
| 3.1 | *Lactobacillus johnsonii* | >99 | 10.1 | *Lactobacillus johnsonii* | >99 |
| 4.1 | *Lactobacillus reuteri* | >99 | 11.1 | *Enterococcus faecium* | >99 |
| 5.1 | *Lactobacillus animalis* | >99 | 12.1 | Mixed culture | -- |
| 6.1 | *Enterococcus faecalis* | >99 | 13.1 | *Lactobacillus animalis* | >99 |
| 7.1 | *Lactobacillus animalis* | >99 | 14.1 | *Lactobacillus reuteri* | >99 |
| 1.2 | *Lactobacillus animalis* | >99 | 9.2 | *Lactobacillus animalis* | >99 |
| 2.2 | *Lactobacillus animalis* | >99 | 10.2 | *Lactobacillus reuteri* | >99 |
| 3.2 | *Lactobacillus animalis* | >99 | 11.2 | *Lactobacillus johnsonii* | >99 |
| 4.2 | *Enterococcus faecalis* | >99 | 12.2 | *Lactobacillus animalis* | >99 |
| 5.2 | *Enterococcus faecalis* | >99 | 13.2 | *Enterococcus faecalis* | >99 |
| 6.2 | *Lactobacillus animalis* | >99 | 14.2 | *Enterococcus faecalis* | >99 |
| 7.2 | *Lactobacillus animalis* | >99 | 15.2 | *Enterococcus faecalis* | >99 |
| 8.2 | *Lactobacillus johnsonii* | >99 | 9.3 | *Lactobacillus plantarum* | >99 |
| 1.3 | *Lactobacillus plantarum* | >99 | 10.3 | *Lactobacillus plantarum* | >99 |
| 2.3 | *Lactobacillus animalis* | >99 | CECT 9859 | *Lactobacillus reuteri* | >99 |
| 4.3 | *Lactobacillus reuteri* | >99 | 12.3 | *Lactobacillus reuteri* | >99 |
| 5.3 | *Lactobacillus animalis* | >99 | 13.3 | *Lactobacillus reuteri* | >99 |
| 6.3 | *Enterococcus avium* | >99 | 14.3 | *Lactobacillus reuteri* | >99 |
| 7.3 | *Lactobacillus reuteri* | >99 | 8.3 | *Lactobacillus reuteri* | >99 |

Strains isolated in this application and identification of their species. *"%Sim."* refers to the percentage similarity.

Figure 4

| | | | | | | | | MICs | | | | | | | | | |
|---|---|---|---|---|---|---|---|---|---|---|---|---|---|---|---|---|---|
| | | Gm | Km | Sm | Tc | Em | Cl | Cm | Am | Nm | Pc | Va | Qda | Lz | Tm | Ci | Ri |
| | MICs EFSA | 8 | 64 | 64 | 32 | 1 | 4 | 4 | 2 | – | – | n.r | – | – | | n.r | – |
| *L. reuteri* | 4.1 | 4 | 32 | 128 | 64 | 0.25 | 0.5 | 16 | 2 | 4 | 1 | >128 | 1 | 2 | >64 | 64 | 0.5 |
| | 14.1 | 0.5 | 16 | 4 | 32 | 0.25 | 0.03 | 8 | 1 | 1 | 1 | >128 | 2 | 2 | 64 | 64 | 0.5 |
| | 10.2 | 1 | 32 | 256 | 16 | 0.5 | 0.12 | 8 | 2 | 1 | 1 | >128 | 4 | 4 | >64 | 64 | 0.5 |
| | 3.3 | 2 | 16 | 256 | 64 | 8 | 16 | 16 | >16 | 2 | >16 | 1 | 4 | 4 | 16 | 2 | 1 |
| | 7.3 | 0.5 | 64 | 128 | 16 | 0.25 | 0.12 | 8 | 4 | 0.5 | 8 | >128 | 4 | 4 | 16 | 64 | 1 |
| | 8.3 | 1 | 32 | 16 | 16 | 0.5 | 0.25 | 8 | 2 | 1 | 2 | >128 | 4 | 4 | 8 | 64 | 1 |
| | CECT 9859 | 0.5 | 32 | 8 | 16 | 0.25 | 0.25 | 8 | 1 | 0.5 | 0.25 | >128 | 4 | 4 | 8 | 64 | 0.5 |
| | 12.3 | 0.5 | 32 | 4 | 32 | 0.5 | 0.06 | 8 | 2 | 0.5 | 8 | >128 | 4 | 4 | 32 | 32 | 1 |
| | 13.3 | 1 | 32 | 16 | 8 | 0.5 | 0.25 | 8 | 1 | 1 | 0.25 | >128 | 4 | 4 | 16 | 64 | 1 |
| | 14.3 | 0.5 | 32 | 16 | 16 | 0.5 | 0.25 | 8 | 1 | 0.5 | 1 | >128 | 4 | 4 | 16 | 64 | 1 |
| | RS1 | 1 | 32 | 8 | 64 | 0.5 | 0,12 | 8 | 2 | 1 | 4 | >128 | 4 | 8 | >64 | 16 | – |
| | MICs EFSA | 16 | 16 | 64 | 4 | 1 | 4 | 4 | 2 | – | – | 2 | – | – | – | n.r | – |
| *L. animalis* | 1.1 | 64 | 256 | >256 | >64 | 4 | >16 | 16 | 1 | >256 | 4 | 4 | >8 | 2 | 0.5 | 1 | 1 |
| | 2.1 | 4 | 256 | 128 | >64 | 0.5 | 0.06 | 16 | 0.12 | 8 | 1 | >128 | 2 | 2 | 0.5 | 1 | 0.5 |
| | 5.1 | 8 | 256 | 256 | 64 | 0.5 | 0.5 | 8 | 0.5 | 8 | 1 | >128 | 4 | 4 | 0.12 | 4 | 0.5 |
| | 7.1 | 8 | 512 | 256 | >64 | 0.5 | 0.25 | 16 | 1 | 16 | 1 | >128 | 2 | 4 | 32 | 2 | 1 |
| | 13.1 | 8 | 256 | 64 | 16 | 0.5 | 0.25 | 8 | 0.5 | 8 | 0.5 | >128 | 2 | 4 | 32 | 2 | 4 |
| | 1.2 | 4 | 128 | >256 | >64 | 0.5 | 0.12 | 16 | 0.5 | 4 | 0.5 | >128 | 2 | 4 | 4 | 2 | 0.5 |
| | 2.2 | 8 | 256 | >256 | >64 | 1 | 0.25 | 16 | 2 | 8 | 2 | >128 | 2 | 4 | 0.12 | 1 | 1 |
| | 3.2 | 4 | 128 | >256 | 64 | 0.5 | 0.5 | 8 | 0.12 | 4 | 1 | >128 | 4 | 2 | 0.5 | 0.5 | 0.5 |
| | 5.2 | 32 | 128 | >256 | 64 | >8 | >16 | 4 | 1 | 256 | 4 | 4 | >8 | 1 | 0.5 | 8 | 8 |

Figure 4 (continued)

| Species | Isolate | Gm | Km | Sm | Nm | Pc | Am | Cm | Cl | Em | Tc | Go | Qda | Lz | Tm | Ci | Ri |
|---|---|---|---|---|---|---|---|---|---|---|---|---|---|---|---|---|---|
| | 6.2 | 8 | 256 | >256 | >64 | 0.5 | 0.25 | 16 | 2 | 8 | 1 | >128 | 1 | 2 | 0.12 | 0.5 | 1 |
| | 7.2 | 4 | 128 | 4 | 64 | 1 | 0.25 | 16 | 8 | >256 | 0.5 | >128 | 2 | 4 | 1 | 2 | 1 |
| | 9.2 | 4 | 256 | >256 | >64 | 1 | 0.25 | 16 | 4 | 8 | 1 | >128 | 2 | 4 | 1 | 2 | 1 |
| | 12.2 | 4 | 256 | 256 | 64 | 0.5 | 0.25 | 16 | 4 | 4 | 1 | >128 | 2 | 8 | 2 | 1 | 1 |
| | 2.3 | 4 | 128 | >256 | >64 | 1 | 0.06 | 8 | 8 | 8 | 2 | >128 | 1 | 2 | 0.5 | 1 | 0.25 |
| | 5.3 | 32 | 128 | >256 | 32 | >8 | >16 | 16 | 4 | 128 | 8 | >128 | >8 | 4 | >64 | 32 | 1 |
| | MICs EFSA | 16 | 16 | n.r | 4 | 1 | 4 | 4 | 2 | – | – | 2 | – | – | – | n.r | – |
| L. johnsonii | 3.1 | 4 | 64 | 64 | 64 | 0.5 | 0.5 | 8 | 1 | 8 | 0.25 | 1 | 1 | 4 | >64 | 128 | 1 |
| | 10.1 | 2 | 64 | 128 | 64 | 0.5 | 1 | 8 | 1 | 8 | 0.12 | 32 | 28 | 8 | >64 | 64 | 1 |
| | 8.2 | 4 | 64 | 64 | 32 | 0.12 | 0.5 | 8 | 1 | 8 | 0.25 | 1 | 1 | 4 | 0.5 | 16 | 1 |
| | 11.2 | 4 | 32 | 32 | 16 | 0.06 | 0.12 | 4 | 1 | 8 | 0.25 | 1 | 2 | 2 | 4 | 16 | 1 |
| | MICs EFSA | 16 | 64 | n.r | 8 | 1 | 4 | 8 | 2 | – | – | n.r | – | – | – | n.r | – |
| L. plantarum | 1.3 | 4 | 64 | 64 | 32 | 1 | 0.25 | 16 | 0.5 | 2 | 1 | >128 | 2 | 8 | 16 | 64 | 1 |
| | 10.3 | 2 | 32 | 32 | 16 | 0.5 | 0.12 | 8 | 1 | 2 | 2 | >128 | 2 | 4 | 16 | 64 | 1 |
| | MICs EFSA | 16 | 64 | n.r | 8 | 1 | 4 | 4 | 4 | – | – | n.r | – | – | – | n.r | – |
| L. murinus | 4.1 | 4 | 128 | 32 | >64 | 0.5 | 2 | 16 | 2 | 4 | 0.25 | >128 | 8 | 4 | >64 | 1 | 4 |
| | 4.11 | 32 | 512 | >256 | >64 | 8 | >16 | 16 | 1 | 16 | 4 | 4 | 8 | 4 | >64 | 16 | 16 |
| | MICs EFSA | 16 | 64 | n.r | 8 | 1 | 4 | 4 | 4 | – | – | n.r | – | – | – | n.r | – |
| L. saerimneri | 4.8 | 16 | 128 | 32 | >64 | >8 | >16 | 8 | 8 | 32 | 4 | >128 | 4 | 2 | >64 | 8 | 2 |
| | 4.9 | 32 | 512 | 256 | 64 | >8 | >16 | 16 | 1 | 128 | 2 | 2 | >8 | 4 | 16 | 2 | 2 |
| | 4.6 | 32 | 512 | 256 | 64 | >8 | >16 | 16 | 1 | 128 | 2 | 2 | >8 | 4 | 16 | 2 | 2 |

MICs (µg/ml) obtained from the differentiated isolates from colostrum milk of Mastín de León bitches. Gm, Gentamicin. Km, Kanamycin. Sm, Streptomycin. Tc, Tetracycline. Em, Erythromycin. Cl, Chloramphenicol, Cm, Clindamycin. Am, Ampicillin. Nm, Neomycin. Pc, Penicillin. Go, Vancomycin. Qda, Quinupristin-Dalfopristin. Lz, Linezolid. Tm, Trimethoprim. Ci, Ciprofloxacin. Ri, Rifampicin. n.r., not required; –, antibiotic is not mentioned by the EFSA.

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| TO<br><br>AQUILON CYL, SL<br>Sanidad Animal - Enfermedades Infecciosas. Fac.<br>Veterinaria. Campus Vegazana, s/n<br>24071 León<br>Spain<br><br>NAME AND ADDRESS<br>OF DEPOSITOR | RECEIPT IN THE CASE OF AN ORIGINAL DEPOSIT issued pursuant to Rule 7.1 by the INTERNATIONAL DEPOSITARY AUTHORITY identified at the bottom of this page |
|---|---|

I. IDENTIFICATION OF THE MICROORGANISM

| Identification reference given by the<br>DEPOSITOR:<br>YogSGR11.3 | Accession number given by the<br>INTERNATIONAL DEPOSITARY<br>AUTHORITY:<br>CECT 9859 |
|---|---|

II. SCIENTIFIC DESCRIPTION AND/OR PROPOSED TAXONOMIC DESIGNATION

The microorganism identified under I was accompanied by:

☒ a scientific description

☒ a proposed taxonomic designation (Mark with a cross where applicable)

III. RECEIPT AND ACCEPTANCE

This International Depositary Authority accepts the microorganism identified under I above, which was received by it on 28th March 2019 (date of the original deposit)[1]

IV. RECEIPT OF REQUEST FOR CONVERSION

The microorganism identified under I above was received by this International Depositary Authority on _____ (date of the original deposit) and a request to convert the original deposit to a deposit under the Budapest Treaty was received by it on _____ (date of receipt of request for conversion)

V. INTERNATIONAL DEPOSITARY AUTHORITY

| Name:<br>COLECCIÓN ESPAÑOLA DE CULTIVOS TIPO (CECT).<br>Address:<br>Edificio 3 CUE.<br>Parc Científic Universitat de Valencia<br>Catedrático Agustín Escardino, 9<br>46980 Paterna (Valencia) ESPAÑA | Signature(s) of person(s) having the power to represent the International Depositary Authority or of authorized official(s):<br><br>Date: 5 Apr 2019<br>Mari Carmen Macián Rovira, PhD |
|---|---|

[1]Where Rule 6.4(d) applies, such date is the date on which the status of international depositary authority was acquired.

Form BP/4 (sole page)

Figure 5: Deposit receipt of CECT 9859

Figure 6

| Race | Sex | Age (yr) | Weight (kg) | Demography Inclusion criteria | Comida | Castrated/sterilized |
|---|---|---|---|---|---|---|
| Mongrel | F | 0,5 | 6,6 | volunteer | feed | No |
| Hound | F | 1 | 5 | Meteorism | feed | No |
| Chiguagua | F | 2 | 3 | Diarrhea | feed | yes |
| Cocker Spaniel | M | 3 | 15 | Capricious appetite | feed | yes |
| Bull Dog | F | 4 | 8,1 | Volunteer | feed | yes |
| Teckel | M | 9 | 7,8 | Frequent dysbiosis | I/D Humeda Hills | No |
| Snauzer | F | 9 | 8 | Inflammatory gastritis | feed | yes |
| Epagneul Bretón | M | 11 | 22 | Cancer receiving chemotherapy, annorexy | feed | No |
| Giant Snauzer | F | 11 | 30,5 | Hypothyroidism, Cusmino Syndrome, Kidney impairment, mammary carcinoma | feed | yes |
| Giant Snauzer | F | 12 | 30 | loose stools | renal feed | yes |
| Mongrel | M | 13 | 30 | Intestinal lymphoma, intermittent diarrhoea every 2-3 days | feed | yes |
| Doberman | F | 4 | 28,5 | loose stools | bacf diet + feed | yes |
| American Stafford | M | 3 | 35 | food allergy and atopy, looking for feed supplement | feed + treats | yes |
| Portuguese Hound | M | 4 | 13,9 | volunteer | metabolic feed | yes |
| Mongrel | F | 6 | 8 | previous week with vomits and diarrhoea | feed | yes |
| Teckel | M | 8 | 9,5 | looking for food supplement | light diet feed | No |
| Retriever/Mast iff | F | 8 | 50 | looking for food supplement | light diet feed | yes |

Dogs participating in the study described in Example 6

FERMENTED MILK PRODUCT FOR ADMINISTRATION IN CANIDS SUCH AS DOGS, AND USES THEREOF

BACKGROUND

Technical Field

The present invention relates to a fermented milk product and a strain that can be used in the production of said milk product. In one embodiment, the present application relates to a fermented milk product that can be fed to a canid, preferably to a dog. In another embodiment, the present invention also refers to the production of a fermented milk product.

Description of the Related Art

Fermented milk products can provide multiple benefits. For example, they are a source of calcium, magnesium, and vitamins and can in addition provide probiotic strains of bacteria. In particular in cases where these bacteria have been isolated from a related animal, they can provide additional benefits, such as an increase in general well-being, inhibition of possibly pathogenic bacteria and thus prevention or treatment of diseases or adverse conditions such as diarrhea.

However, it was commonly believed that fermented milk products are not suitable for the administration to canids as, e.g., dogs can be intolerant to lactose. It was also unclear at the time of the invention whether a fermented milk product would be voluntarily eaten by canids such as dogs and is thus feasible as a probiotic.

BRIEF SUMMARY

The present inventors have identified a *Lactobacillus reuteri* strain from dog colostrum (deposited with the Spanish Type Cultures Collection as CECT 9859) that has highly beneficial properties and can be used to produce a fermented milk product. Due to the origin of strain CECT 9859, the administration of a fermented milk product produced with strain CECT 9859 is particularly beneficial for canids, e.g., dogs. It has been demonstrated that the strains identified herein and in particular strain CECT 9859 can inhibit the growth of potentially pathogenic bacteria. Strain CECT 9859 additionally has a very low antibiotic resistance and allows for a very short culturing time in the production of a fermented milk product.

In addition, the present inventors have surprisingly found that a fermented milk product created with a bacterial strain isolated from dog is voluntarily eaten by canids such as dogs. Furthermore, it has been found that fermented milk products according to the invention do not lead to negative effects such as diarrhea. It was furthermore demonstrated that fermented milk products can improve overall well-being of treated animals, in particular dogs, and, e.g., improve the shininess of the coat (a general indication of good health) and an increase in vigor. The present inventors have furthermore found that strain CECT 9859 can be used to produce a fermented milk product with a very low lactose content and in very short time.

Thus, fermented milk products produced with the strain identified in the present invention are highly beneficial for the administration to canids, for example dogs.

BRIEF DESCRIPTION OF THE SEVERAL VIEWS OF THE DRAWINGS

FIG. 1 shows the animals behavior when offered a fermented milk product over the course of the first seven consecutive days of the study. Column A shows the number of dogs that immediately ate the offered fermented milk product. Column B shows the number of dogs that first explored the fermented milk product and immediately ate it. Column C shows the number of dogs that smelled at the fermented milk product and ate it after a short time. Column d shows the number of dogs that recognized the fermented milk product but did not eat it. As can be seen in the figure, most dogs immediately ate the fermented milk product when first confronted therewith and this number increased even further after the first day of the study.

FIG. 2 shows the amount of fermented milk product eaten by the dogs at the first seven consecutive days of the study. Column A shows the number of dogs that ate all the offered fermented milk product. Column B shows the number of dogs that started eating but did not eat all of the offered fermented milk product. Column C shows the number of dogs that tasted the fermented milk product but did not eat it. Column D shows the number of dogs that smelled at the fermented milk product but did not taste it. As can be seen, most dogs ate all of the fermented milk product.

FIG. 3 is an overview of strains identified in this application and the species they were classified as. As can be seen, CECT 9859 is of the genus *Lactobacillus reuteri*.

FIG. 4 shows the resistance of the identified strains to different antibiotics. The values represent the minimum inhibitory concentration (MIC) in μg/ml against specific antibiotics, obtained in accordance with "*Guidance on the assessment of bacterial susceptibility to antimicrobials of human and veterinary importance*," EFSA Panel on Additives and Products or Substances used in Animal Feed (FEEDAP), European Food Safety Authority (EFSA), Parma, Italy. EFSA Journal 2012; 10(6):2740. The smaller the MIC, the less resistance the strain is against the tested antibiotics. The cut-off values according to the EFSA for the specific species are also shown. According to the EFSA, bacterial strain is defined as susceptible when it is inhibited at a concentration of a specific antimicrobial equal or lower than the established cut-off value and is defined as resistant when it is not inhibited at a concentration of a specific antimicrobial higher than the established cut-off value.

FIG. 5 shows the receipt of the deposit for strain CECT 9859.

FIG. 6 shows an overview of the dogs participating in the study described in Example 6.

DETAILED DESCRIPTION

The following detailed description discloses specific and/or preferred variants of the individual features of the invention. The present invention also contemplates as particularly preferred embodiments those embodiments, which are generated by combining two or more of the specific and/or preferred variants described for two or more of the features of the present invention.

Unless expressly specified otherwise, the term "comprising" is used in the context of the present document to indicate that further members may optionally be present in addition to the members of the list introduced by "comprising," It is, however, contemplated as a specific embodiment of the present invention that the term "comprising" encompasses the possibility of no further members being present, i.e., for the purpose of this embodiment "comprising" is to be understood as having the meaning of "consisting of."

Unless expressly specified otherwise, all indications of relative amounts in the present application are made on a weight/weight basis. Indications of relative amounts of a component characterized by a generic term are meant to refer to the total amount of all specific variants or members covered by said generic term. If a certain component defined by a generic term is specified to be present in a certain relative amount, and if this component is further characterized to be a specific variant or member covered by the generic term, it is meant that no other variants or members covered by the generic term are additionally present such that the total relative amount of components covered by the generic term exceeds the specified relative amount; more preferably no other variants or members covered by the generic term are present at all.

The Milk Product of the Present Invention

The fermented milk product of the present invention, hereinafter also referred to as the milk product, is not particularly limited. The fermented milk product according to the present invention means a feed or feed additive product which is produced in a method comprising the fermentation of a milk base with a bacterium, preferably a lactic acid bacterium. The fermented milk product according to the present invention also encompasses a feed or feed additive product which is produced in a method comprising the fermentation of a milk base with at least two different strains of bacteria, wherein preferably one, more preferably two, and most preferably all bacteria are lactic acid bacteria. The fermented milk product includes a thermophilic fermented milk product. Additional steps can be performed after the fermentation, such as straining, stirring, settling etc.

The term milk base is not particularly limited and includes any milk material that can be fermented in accordance with the present invention, such as milk, milk suspensions, whey protein concentrate, cream, milk powder, or buttermilk. Preferably, the milk base is milk.

The milk used in the production of the fermented milk product can be any kind of milk produced by a mammal. Preferably, the milk is from cow, sheep, goat, water buffalo, horse, camel, donkey, reindeer, or yak. Most preferably, the milk is from a cow.

The milk used in the production of the fermented milk product can for example be homogenized, pasteurized, lactose free or raw. Preferably, the milk is homogenized and pasteurized.

The term "homogenized" as used in the present invention means that the treated composition, e.g., a liquid, was mixed intensively in order to obtain a soluble suspension or emulsion. Methods for homogenization are known in the art. The term "pasteurized" as used in the present invention means that the treated composition, e.g., a liquid, underwent a treatment to reduce or eliminate live microorganisms present in the treated composition. Methods for pasteurization are known in the art and, e.g., comprise heating the composition to a certain temperature and maintaining said temperature for a certain time, optionally followed by rapid cooling.

The milk used in the production of the fermented milk product can for example be whole milk, low fat milk (usually with about 1% to about 2% of fat), or fat free milk such as skim milk. Preferably, the milk is whole milk.

Most preferably, the milk base used in the production of the fermented milk product is homogenized and pasteurized whole milk from a cow.

The fermented milk product comprises bacteria (i.e., live or dead bacteria) that were used in the fermentation process, e.g., bacteria of strain CECT 9859.

In one embodiment, the fermented milk product comprises dead (i.e., inactivated) bacteria selected from any of the bacteria disclosed herein, more preferably dead bacteria wherein the bacteria were also used for fermentation, and most preferably dead bacteria of strain CECT 9859. A fermented milk product according to the present invention comprising dead bacteria can provide beneficial effects to animals. For example, a such a milk product can comprise substances such as reuterin released by the bacteria. In addition, it can also comprise antigenic compounds and/or compounds that have a beneficial effect in the gut in particular when coming into contact with the animal's mucosa. The bacteria can be inactivated by methods known to the person skilled in the art, e.g., pasteurization. For example, the bacteria can be inactivated by heating at a temperature of 65° C. for 88 minutes.

Preferably, the fermented milk product comprises live bacteria, preferably live bacteria selected from any of the bacteria disclosed herein, more preferably live bacteria wherein the live bacteria were also used for fermentation, and most preferably live bacteria of strain CECT 9859. In a particular embodiment, the fermented milk product comprises live bacteria of strain CECT 9859 and another strain of live bacteria, wherein said second strain of live bacteria is preferably a strain from the genus *Streptococcus*, more preferably *Streptococcus thermophilus*. The ratio of cfu of these two strains in the fermented milk product may for example be 100:1 to 1:1, preferably 50:1 to 2:1, more preferably 25:1 to 4:1, even more preferably 15:1 to 6:1, even more preferably 12:1 to 8:1, and most preferably 9:1 cfu of the first type of live bacteria, preferably from strain CECT 9859, to the second type of life bacteria, preferably from the genus *Streptococcus*, more preferably from *S. thermophilus*. In another particular embodiment, the fermented milk product additionally comprises live bacteria of a third strain, wherein said third strain of live bacteria is preferably a strain from the genus *Lactobacillus*, more preferably *Lactobacillus delbrueckii* subsp. *bulgaricus*, also known as *Lactobacillus bulgaricus*. The ratio of cfu of these three strains in the fermented milk product may for example be 6:3:1 (CECT 9859: *L. delbrueckii: S. thermophilus*). Preferably, the ratio is 6:3:1 when the concentration of a starter culture is 1-2×10$^8$ cfu/ml and the volume of starter culture to be added to the fermentation culture is about 1% (v/v) of the total fermentation culture. In another particular embodiment, the fermented milk product additionally comprises live bacteria of a fourth, fifth and/or sixth strain or any number of additional strains.

The pH of the fermented milk product is not particularly limited. The pH of the fermented milk product may be from about 4.9 to about 4.0, preferably from about 4.7 to about 4.2, more preferably from about 4.6 to about 4.2, and even more preferably from about 4.6 to about 4.5. The pH of the fermented milk product may also be below 5.0, preferably below 4.8, more preferably below 4.7, and most preferably below 4.6. The fermented milk product may have a pH of 5.0, 4.9, 4.8, 4.7, 4.6, 4.5, 4.4, 4.3, 4.2, 4.1, or 4.0.

The lactose content of the fermented milk product is preferably low. In one embodiment, when the milk base has a lactose content of 4.8 g/100 ml, the fermented milk product can have a lactose content of 3.65 g/100 ml. The fermented milk product may have a lactose content of at least 0.5 g/100 ml, preferably at least 1 g/100 ml, more preferably at least 2 g/100 ml, even more preferably at least 3 g/100 ml, and most preferably at least 3.5 more preferably at least 2 g/100 ml. The fermented milk product may have a lactose content of at most 25 g/100 ml, preferably at most 15 g/100 ml, more preferably at most 8 g/100 ml, even more preferably at most 5 g/100 ml, and most preferably at most 4 g/100 ml. The lactose content of the fermented milk product can be between 0.5 and 25 g/100 ml, preferably between 1 and 15 g/100 ml, more preferably between 2 and 8 g/100 ml, even more preferably between 3 and 5 g/100 ml, and most preferably between 3.5 and 4 g/100 ml. In a particular embodiment, the lactose content is about or is 3.65 g/100 ml. The lactose content can further be a within any combination of the above values.

The fermented milk product can preferably be stored for a certain time. For example, the fermented milk product can be stored at a temperature of 4-8° C. (e.g., in a fridge) for at least 7 days, preferably for at least 14 days, more preferably for at least 20 days, even more preferably for at least 30 days, and most preferably for at least 45 days. The fermented milk product can preferably be stored at −20° C. (e.g., in a freezer) for at least 2 weeks, preferably for at least four weeks, more preferably for at least two months, and most preferably for at least 3 months. Preferably, the amount of colony forming units (cfu) of lactic acid bacteria per ml fermented milk product after said storage time is at least 20%, more preferably at least 50%, most preferably at least 70% of the cfu of lactic acid bacteria per ml fermented milk product before storage. Alternatively, the amount of colony forming units (cfu) of lactic acid bacteria of strain CECT 9859 per ml fermented milk product after said storage time is at least 20%, more preferably at least 50%, most preferably at least 70% of the cfu of lactic acid bacteria of strain CECT 9859 per ml fermented milk product before storage. Preferably, the fermented milk product can be stored in the same way that it is served to the animal, i.e., it can be fed to the animal without further treatment. In another embodiment, the fermented milk product can be stored in a way that it can be fed to the animal without further treatment except for a step of thawing the frozen fermented milk product.

The fermented milk product of the present invention can be in any form, for example be in liquid form or solid form. The fermented milk product of the present invention can for example be frozen or freeze dried and/or pulverized.

The fermented milk product of the present invention also comprises a fermented milk product produced by any of the methods disclosed herein.

Uses of the Fermented Milk Product of the Present Invention

The present invention also provides the use of the fermented milk product of the present invention in a method of treating an animal, preferably a canid, more preferably a canine, most preferably a dog. The present invention also provides the use of the fermented milk product of the present invention for the manufacture of a medicament for treating an animal, preferably a canine, most preferably a dog. The present invention also provides the use of the fermented milk product of the present invention for use in a method of treating an animal, preferably a canine, most preferably a dog. For example, the fermented milk product can be used to treat diarrhea. In one embodiment, the fermented milk product can be used to treat and/or prevent unspecific diarrhea associated to the use of antibiotics. In another embodiment, the fermented milk product can be used to treat and/or prevent gastroenteritis, for example giardiosis (infection for *Giardia lamblia*), bacterial gastroenteritis (*Salmonella, E. coli*) or viral-parvovirosis. In another embodiment, the fermented milk product can be used to treat ingestion of foreign bodies, especially in puppies. In another embodiment, the fermented milk product can be used to help in the recovery from parasitosis, e.g., by *Toxocara*, Toxascaris and/or Coccidia. In another embodiment, the fermented milk product can help during diet changes. In another embodiment, the fermented milk product can help with recovery from anesthesia, e.g., after surgery. In another embodiment, the fermented milk product can be used to treat and/or prevent alimentary allergies. In another embodiment, the fermented milk product can be used to support recovery from poisoning. In another embodiment, the fermented milk product can be used to treat dysbiosis, i.e., an abnormal microbiotic composition. In another embodiment, the fermented milk product can be co-administered with compounds known to cause dysbiosis, for example as a side effect.

The present invention also provides methods for treating and/or preventing any of the above conditions and diseases, optionally in an animal, preferably a canine, most preferably a dog.

In the present invention, the term canid refers to a member of the biological family Canidae, e.g., to a fox, a jackal, a wolf or a dog. In the present invention, the term canine refers to a member of the genus *Canis*, e.g., a wolf or a dog. In the present invention, the term dog refers to a domestic dog, i.e., to a member of the genus *Canis lupus familiaris*, sometimes also named *Canis familiaris*.

The present invention also provides the use of the fermented milk product of the present invention in a method of increasing the shininess of the coat, increasing vigor, and/or increasing vitality of an animal, preferably a canid, more preferably a canine, most preferably a dog. Furthermore, the present invention also provides the use of the fermented milk product of the present invention as an animal feed or feed additive, preferably a canid feed or feed additive, more preferably a canine feed or feed additive, most preferably a dog feed or feed additive.

Methods for Producing the Fermented Milk Product of the Present Invention

The present invention also provides fermentation methods and methods for producing the fermented milk product of the present invention. Fermentation as used in the present invention refers to the conversion of carbohydrates into acids or alcohols achieved by the cultivation of at least one microorganism. For example, in the fermentation of the fermented milk product according to the present invention, lactose can be converted into lactic acid by the cultured microorganisms.

In one embodiment, methods of fermentation include co-cultivation of a lactic acid bacterium, e.g., a *Lactobacillus* strain, according to the present invention with another lactic acid bacteria strain, preferably a strain from the genus *Streptococcus*, more preferably *Streptococcus thermophilus*. Preferably the additional strain is a thermophile strain, i.e., is able to grow and ferment at high temperatures. Strains of *Streptococcus thermophilus* that can be used for the preparation of a fermented milk product are known in the art and commercially available. For example, Danisco® TA 40 LYO is a thermophilic culture of *Streptococcus thermophilus* that can be used with any of the embodiments described herein. For the starting culture, exemplary ratios (in cfu) of strains for co-cultivation may be 100:1 to 1:1, preferably 50:1 to 2:1, more preferably 25:1 to 4:1, even more preferably 15:1 to 6:1, even more preferably 12:1 to 8:1, and most preferably 9:1 cfu of the *Lactobacillus* strain to cfu of the *Streptococcus* strain.

In another particular embodiment, methods of fermentation also include co-cultivation with a third lactic acid bacterium, preferably a strain from the genus *Lactobacillus*, more preferably *Lactobacillus delbrueckii* subsp. *bulgaricus*, also known as *Lactobacillus bulgaricus*. For the starting culture, exemplary ratios (in cfu) of strains for co-cultivation may be 6:3:1 (CECT 9859: *L. delbrueckii: S. thermophilus*). Preferably, the ratio is 6:3:1 when the concentration of a starter culture is 1-2×10⁸ cfu/ml and the volume of starter culture to be added to the fermentation culture is about 1% (v/v) of the total fermentation culture.

In another particular embodiment, methods of fermentation also include co-cultivation with a fourth, fifth and/or sixth strain or any number of additional strains.

It is believed that co-cultivation of a bacterial strain according to the present invention with the additional bacterial strain, preferably a strain from the genus *Streptococcus*, more preferably *S. thermophilus*, is beneficial. In particular, it is known from the production of yoghurt that for example *S. thermophilus* and *Lactobacillus* strains show synergistic effects. For example, it is believed that *S. thermophilus* provides *Lactobacillus* strains with folic acids and formic acids and in addition leads to a reduction of the oxygen content in the culture, especially in early phases. *Lactobacillus* strains on the other hand are believed to have a strong proteolytic activity and thus lead to increased amounts of amino acids and peptides in the culture which increases *S. thermophilus* growth.

In one embodiment, the method for producing the fermented milk product of the present invention comprises the following steps:

Adding to a milk base a starter culture of lactic acid bacteria comprising at least one strain of lactic acid bacteria, wherein said strain is optionally isolated from a canid, preferably from a canine, more preferably from a dog, even more preferably from dog colostrum or milk, and most preferably from dog colostrum, wherein said strain is preferably from the genus *Lactobacillus*, more preferably from the genus *Lactobacillus reuteri*, and most preferably the strain deposited with the Spanish Type Cultures Collection as CECT 9859; wherein optionally, said starter culture may further comprise a second strain of lactic acid bacteria, preferably a strain from the genus *Streptococcus*, most preferably *Streptococcus thermophilus*, for example the strain of Danisco® TA 40 LYO;

Fermenting the milk base until a desired pH is reached, wherein said desired pH is preferably from about 4.9 to about 4.0, more preferably from about 4.7 to about 4.2, even more preferably from about 4.6 to about 4.2, even more preferably from about 4.6 to about 4.5, and most preferably about 4.6;

Obtaining the fermented milk product, and

Optionally packaging the fermented milk product.

In one embodiment, the method for producing the fermented milk product of the present invention comprises the following steps:

(a) inoculating milk with a starter culture comprising CECT 9859 and, optionally, a *S. thermophilus* strain; and (b) incubating the inoculated milk at 30-43° C. until a pH of 5.0 or less is reached.

In one embodiment, the method for producing the fermented milk product of the present invention comprises the following steps:

(a) inoculating milk with a starter culture comprising CECT 9859 and, optionally, a *S. thermophilus* strain; and (b) incubating the inoculated milk at 30-43° C. until a pH of 4.6 or less is reached.

In one embodiment, the method for producing the fermented milk product of the present invention comprises the following steps:

(a) inoculating milk with a starter culture comprising CECT 9859 and, optionally, a *S. thermophilus* strain; and (b) incubating the inoculated milk at 36-38° C. until a pH of 4.6 or less is reached.

In one embodiment, the method for producing the fermented milk product of the present invention comprises the following steps:

(a) inoculating milk with a starter culture comprising CECT 9859 and, optionally, a *S. thermophilus* strain; and (b) incubating the inoculated milk at 37° C. until a pH of 4.6 or less is reached.

In some embodiments, the ratio of CECT 9859 to *S. thermophilus* in the starter culture is 9:1. In some embodiments, the *S. themophilus* strain is Danisco® TA 40 LYO.

It is to be understood that any of the above methods encompasses methods wherein a starter culture comprising both CECT 9859 and a *S. thermophilus* strain is used to inoculate the milk as well as embodiments where a starter culture comprising CECT 9859 and a further starter culture comprising a *S. thermophilus* strain are used to inoculate the milk.

In one embodiment, the method for producing the fermented milk product of the present invention comprises the following steps:

(a) inoculating milk with a starter culture comprising CECT 9859 and a *S. thermophilus* strain, preferably Danisco® TA 40 LYO; and (b) incubating the inoculated milk at 37° C. until a pH of 4.6 or less is reached.

In some embodiments, the milk that is to be inoculated with the one or more starter cultures is pasteurized cow milk. In some embodiments, the ratio of CECT 9859 to the *S. thermophilus* strain with which the milk is inoculated is 9:1.

Strains of the Present Invention

The strains for use according to the present invention are not particularly limited, as long as the strains are suitable to produce a fermented milk product. The microorganisms, preferably bacteria, that can be used according to the invention are microorganism with beneficial effects. They are preferably lactic acid bacteria.

Lactic acid bacteria (LAB) comprise a clade of Gram-positive, acid-tolerant bacteria that are associated by their common metabolic and physiological characteristics. These bacteria, naturally found in decomposing plants and lactic products, as well as in animal feces, produce lactic acid as a major metabolic end-product of carbohydrate fermentation. Lactic acid bacteria are generally recognized as safe (GRAS status), due to their ubiquitous appearance in food and their contribution to the healthy microflora of mammalian mucosal surfaces. Lactic acid bacteria are preferably selected among the genera *Lactobacillus, Leuconostoc, Pediococcus, Lactococcus, Streptococcus, Aerococcus, Carnobacterium, Enterococcus, Oenococcus, Sporolactobacillus, Tetragenococcus, Vagococcus, and Weisella. Lactobacillus* and/or *Enterococcus* may be preferred, and *Lactobacillus* may be even more preferred. The bacteria used herein are preferably Gram positive and are catalase negative. Whether a bacterium is Gram positive can be tested according to standard technologies known in the art. Gram staining consists in consecutive staining with different "colorings" (stains) and washing of the sample in order to check if it is positive or negative. Whether a bacterium is catalase negative is tested as follows: The catalase test involves adding hydrogen peroxide to a culture sample or agar slant. If the bacteria in question produce catalase, they will convert the hydrogen peroxide and oxygen gas will be evolved. The evolution of gas causes bubbles to form and these bubbles are indicative of a positive test (catalase positive bacterium).

The lactic acid bacteria preferred herein are preferably able to grow in MRS medium, and more preferably in non-acidified MRS agar as described below. MRS medium was created for favoring the growth of lactic acid bacteria, especially *Lactobacillus* sp. It is believed to disfavor the growth of the vast majority of Gram-negative bacteria. However, other bacteria than lactic acid bacteria may eventually grow in MRS, and it is therefore recommendable or even necessary to check that the colonies belong to Gram positive and are catalase negative bacteria.

The lactic acid bacteria preferred herein may possibly be probiotic bacteria. The most commonly accepted definition of "probiotic" was given in 1998 by Fuller, who described it as "a live microbial feed supplement which beneficially affects the host animal by improving its intestinal microbial balance," Generally, probiotics are live microorganisms. It is believed that different probiotics have different actions in the gut, and different probiotics may therefore act together to provide a beneficial effect. Other sources define probiotics as those microorganisms for which a health benefit on the human or animal has already been proven. Selection criteria for probiotics are published in: "Report of a Joint FAO/WHO Expert Consultation on Evaluation of Health and Nutritional Properties of Probiotics in Food Including Powder Milk with Live Lactic Acid Bacteria," Food and Agriculture Organization of the United Nations and World Health Organization, 2001, Cordoba, Argentina. The advantages of the use of live bacteria have been widely described.

The lactic acid bacteria strains that can be used according to the invention are preferably of canid origin, more preferable of canine origin, and even more preferably from a dog. Even more preferably, the strains have been isolated from dog milk or dog colostrum. Most preferably, the strains have been isolated from dog colostrum.

Strains of canid, preferably of canine and even more preferably of dog origin are particularly preferable as these strains also naturally occur in canids such as dogs. Lactic acid bacteria living in guts of different species differ significantly, especially if the species are not closely related. Thus, lactic acid bacteria for the treatment of a certain animal should be isolated from a closely related species and ideally from an animal of the same species, as such strains are adapted to live in the specific gut biome of said treated animal. Such strains are believed to more readily colonialize the gut of the treated animal and provide more beneficial effects with less or no undesired side-effects.

It is beneficial if the strains were isolated from milk or more preferably from colostrum. Colostrum strains are naturally selected to colonize the guts of newborn mammals, which are sterile at the moment of birth. They contribute to not only define early microbiota but also to build immunological competence (Maynard et al., 2012. *Nature.* 489 (7415): 231-241; Rodriguez et al., 2015. *Microb Ecol Health Dis.* 26: 26050; Redfern & Suchodolski, 2017. Vet Rec. 181(14): 370). On the other hand, bacteria isolated from for example feces are a surrogate of what is in the gut at a given moment and are indicative of the equilibrium in the microbiota at a specific moment, i.e., are a result of the diet and natural history of a particular individual. For example, pathological bacteria can be found in feces, whereas bacteria from colostrum are in general beneficial. In a particular preferred embodiment, the strains of the present invention are isolated from dog colostrum.

In the most preferred embodiment, the strain used in the production of the fermented milk product according to any of the embodiments described herein is the strain deposited under the Budapest treaty with deposit number CECT 9859 by Aquilon Cyl, SL, the applicant of the present invention, which was deposited on 28 Mar. 2019 with the Spanish Type Cultures Collection (Colección Española de Cultivos Tipo (CECT)), with the following address:

Colección Española de Cultivos Tipo (CECT)
Edificio 3 CUE,
Parc Científic Universitat de València,
Catedrático Agustin Escardino, 9,
46980 Paterna (Valencia) SPAIN
The receipt of the deposit is shown in FIG. 5.

Activity Against Undesired Bacteria

The present invention uses microorganisms, in particular bacteria, and preferably lactic acid bacteria, which have a potential of showing a health benefit on animals, in particular canids, more preferably canines, and even more preferably dogs. For example, a health benefit can be provided by lactic acid bacteria inhibiting the growth of undesired, e.g., pathogenic, bacteria.

The activity against the undesired bacteria is tested according to the spot on lawn test, which is described in the following. Liquid overnight cultures (MRS) of each strain to be tested are applied as single spots of 10 μl on MRS agar and incubated at 39° C. for 24 h under anaerobic conditions. After incubation, the plates are covered with 10-15 ml of semi-solid BHI agar (0.7%) inoculated with one of the undesired bacteria (1%; 1 ml overnight culture in 100 ml medium). Separate plates containing one particular strain to be tested are overlaid with one of the undesired bacteria species, respectively. Each such test is performed in triplicate. After incubation for 24 h at or near the optimal growth temperature of the undesired bacterium (which optimal growth temperature is known in the art for each of the undesired bacteria referred to herein, e.g., 37° C. for *E. coli*), the samples are examined for evidence of inhibition. To that end it is first checked if an inhibition zone is present. If so, the diameter of the inhibition zone is measured optically. In events where the inhibition zone appears not exactly circular the measurement of the inhibition zone is done with a rule of measuring the inhibition zone's shortest diameter. Finally, the arithmetic mean of the triplicate experiment is determined. This mean is then used as the size of the inhibition zone against the tested undesired bacteria.

Alternatively, the agar well diffusion assay may be used for determining inhibition zones. This process eliminates any traces of lactic acid that could be produced in low glucose MRS broth by neutralizing cell-free supernatants. Stationary phase cultures of the species to be tested, grown under anaerobic conditions, are harvested by centrifugation (5000 g/20 min/4° C.), and the pH of the cell-free supernatant is adjusted to 6.5 with 1M NaOH. Supernatants are filter-sterilized (0.20 mm; Millipore Ltd., Hertfordshire, England). The cell-free supernatant (30 μl) is added to 7-mm diameter wells cut into agar plates inoculated with [approximately] 105 colony-forming units (CFU)/ml of the undesired bacterium listed in (i), (ii), (iii), (iv). The agar plates are then incubated at 30° C. for 24 hours. Finally, the diameter of the inhibition zones around the wells is measured.

The assays above are based on what has been described by Kawai et al., 2004. Applied and Environmental Microbiology 70(5): 2906-2911; Dortu et al. 2008. Letters in Applied Microbiology, 47: 581-586; Hata et al., 2009. International Journal of Food Microbiology, 137: 94-99, Awaisheh 2009. Food Pathogens and Disease 6 (9): 1125-1132.).

In one embodiment, the inhibition zone for *E. coli* of a strain of the present invention determined by any of the above methods is at least 9 mm, more preferably at least 10 mm, even more preferably at least 11 mm, even more preferably at least 12 mm, even more preferably at least 13 mm, even more preferably at least 14 mm, even more preferably at least 15 mm, even more preferably at least 16 mm, even more preferably at least 17 mm, even more preferably at least 18 mm, even more preferably at least 19 mm, even more preferably at least 20 mm, even more preferably at least 21 mm, even more preferably at least 22 mm, even more preferably at least 23 mm, even more preferably at least 24 mm, and most preferably at least 25 mm.

In a particular embodiment, the inhibition zone for *E. coli* of a strain of the present invention determined by the spot on lawn test is at least 18 mm, more preferably at least 25 mm.

Antibiotic Resistance Profile

Optionally, any of the strains disclosed herein are additionally tested for their antibiotic resistance profile, e.g., by the Minimal antibiotic concentration test (VetMIC microplate tests) and/or a genotypic resistance test is performed by performing a PCR for different resistance genes (Egervärn et al., 2010. Antonie van Leeuwenhoek 97: 189-200). It is believed that bacteria with no antibiotic resistance (absence or inactivity/loss-of-function of resistance genes) are most suited for application to dogs.

For the purpose of distinguishing resistant from susceptible strains, the European Food Safety Authority (EFSA) Panel on Additives and Products or Substances used in Animal Feed (FEEDAP) defines microbiological cut-off values. Microbiological cut-off values are set by studying the distribution of MICs of the chosen antimicrobials in bacterial populations belonging to a single taxonomical unit (species or genus). The part of the population that clearly deviates from the normal susceptible populations is categorized as resistant. The microbiological cut-off values that may be used for evaluating the antibiotic resistances of the strains of the present invention are the ones defined in the "*Guidance on the assessment of bacterial susceptibility to antimicrobials of human and veterinary importance*," EFSA Panel on Additives and Products or Substances used in Animal Feed (FEEDAP), European Food Safety Authority (EFSA), Parma, Italy. EFSA Journal 2012; 10(6):2740. According to the EFSA, bacterial strain is defined as susceptible when it is inhibited at a concentration of a specific antimicrobial equal or lower than the established cut-off value and is defined as resistant when it is not inhibited at a concentration of a specific antimicrobial higher than the established cut-off value. For example, the strains can be tested against the following antibiotics: Gentamicin, Kanamycin, Streptomycin, Erythromycin, Clindamycin, Tetracycline, Chloramphenicol, Neomycin, Ampicillin, Penicillin, Vancomycin, Quinupristin-Dalfopristin, Ciprofloxin, Trimethoprim, Linezolid and/or Rifampicin.

In a preferred embodiment, the strains according to the present invention meet the above described cut-off values of the EFSA (i.e., are classified as susceptible) for at least one, at least two, at least three, at least four, at least five, at least six, at least seven, at least eight, at least nine, at least ten, at least eleven, at least twelve, at least thirteen, at least fourteen, at least fifteen, at least sixteen, at lease seventeen, or at least eighteen of the following antibiotics: Gentamicin, Kanamycin, Streptomycin, Erythromycin, Clindamycin, Tetracycline, Chloramphenicol, Neomycin, Ampicillin, Penicillin, Vancomycin, Quinupristin-Dalfopristin, Ciprofloxin, Trimethoprim, Linezolid and Rifampicin.

Fermentation Time

The lactic acid bacteria strains of the present invention allow for a short fermentation time during the production of the milk product. This is highly beneficial, as it decreases the time needed for production, decreases production costs, and decreases energy consumption during the production process. A further major benefit of the reduced time needed for fermentation is that the production process can be performed within a single labor day, which also ensures quick and cheap production. In addition, it has been found that the lactic acid bacteria strains of the present invention allow for an even shorter cultivation time when moving from a small-scale fermentation to a large scale fermentation. For example, it was found by the present inventors that when moving from a small scale 250 ml fermentation to a large scale 2001 fermentation, the fermentation time decreases by about 15%. Thus, the lactic acid bacteria strains of the present invention are particularly suitable for large scale production of milk products.

Other Benefits

The lactic acid bacteria strains of the present invention are believed to have additional benefits. For example, it is believed that the lactic acid bacteria strains of the present invention produce bacteriocins, for example reuterin. Bacteriocins such as reuterin are antimicrobial compounds. Strains producing bacteriocins such as for example reuterin are particularly useful as probiotics, as, e.g., reuterin inhibits the growth of many bacteria, yeasts, molds, and protozoa without killing beneficial bacteria of the gut.

In addition, it is believed that the lactic acid bacteria strains of the present invention produce beneficial compounds such as vitamins and have particularly a beneficial protein profile. Exemplary compounds that are believed to be produced by the strains of the present invention include but are not limited to vitamin B2, vitamin B6, vitamin B12, folic acid, niacin, and pantothenic acid.

Optionally, any of the lactic acid bacteria strains disclosed herein can also be tested for their adherence to epithelial surfaces and persistence in the animal (e.g., dog) gastrointestinal tract. It is believed that strains with good adherence properties will perform best. In general, *L. reuteri* strains are known to be able to colonize the gastrointestinal tract, and it is believed that, e.g., strain CECT 9859 performs well in this regard.

Optionally, any of the lactic acid bacteria strains disclosed herein can also be tested for acid and bile resistance, which ensures that the bacteria survive the oral intake. In general, *L. reuteri* strains are known to perform well in this regard, and it is believed that, e.g., strain CECT 9859 also shows a high acid and bile resistance.

Administration of the Milk Product of the Present Invention

The fermented milk product of the present invention can be administered to an animal, preferably to a mammal, more preferably to a canid (e.g., a fox, a jackal, a wolf or a dog), even more preferable to a canine, i.e., a member of the genus *Canis* (e.g., a wolf or a dog), and most preferably to a dog. The dog may be a young or an adult dog.

In a particular embodiment, the animal to which the milk product of the present invention is administered can be intolerant to lactose. In a particular embodiment, the tolerance limit of the animal, for example an adult dog for lactose is 1-2 g lactose/kg animal weight and day.

Any number of servings of the milk product of the present invention may be administered and the skilled person can choose the length of the treatment according to the needs of the respective animal. In a particular embodiment the total number of the milk product of the present invention administered to an animal is at least 1, at least 2, at least 3, at least 4, at least 5, at least 10, at least 20, at least 30, at least 40, at least 50, at least 100, at least 200, at least 300, at least 400, at least 500, or at least 1000 servings. In one embodiment, the milk product of the present invention is administered between 1 and 4 weeks, or between 2 and 3 weeks, or for 2 weeks, or for 15 days. In a preferred embodiment the milk product of the present invention is administered continuously for at least five days or during the entire animal's life. In another preferred embodiment, the milk product is administered continuously from the age of two weeks, from the age of three weeks, from the age of four weeks, from the age of five weeks, from the age of six weeks, from the age of seven weeks, or from the age of eight weeks, and preferably to the end of the animal's life. In one embodiment, the milk product is administered to an animal of at least two years of age. In another preferred embodiment, the milk product is administered continuously from weaning to the end of the animal's life.

The number of administrations of the milk product of the present invention is not particularly limited. In a particular embodiment the milk product of the present invention can be administered once or several times a month, e.g., 1, 2, 3, or 4 times a month. In another particular embodiment the milk product of the present invention can be administered once or several times a week, e.g., 1, 2, 3, 4, 5, 6, or 7 times a week. In another particular embodiment the milk product of the present invention can be administered once or several times a day, e.g., 1, 2, 3, 4, 5, or 6 times a day. In the most preferred embodiment, the milk product of the present invention is administered once daily.

The Milk product according to the present invention may be administered orally. The milk product of the present invention can be administered as a mixture together with food or water or can be administered without any additional food or water. In a particularly preferred embodiment, the milk product of the present invention is administered without any additional food or water. In a particularly preferred embodiment, the milk product of the present invention is administered between meals when the animal is not offered any food other than the milk product of the present invention.

The amount of milk product of the present invention administered per serving is not particularly limited. In one particular embodiment, the amount of milk product of the invention administered per serving will depend on the weight or size of the animal. For example, between 0.5 and 200 ml/kg. preferably between 1 and 100 ml/kg, more preferably between 2 and 50 ml/kg, even more preferably between 5 and 20 ml/kg, even more preferably about 10 ml/kg, and most preferably 10 ml/kg can be administered per serving.

In one particular embodiment, the following amounts are administered per serving to a dog of a certain weight, preferably once a day, and preferably to a dog:

TABLE 1

| Exemplary Administration Amounts for Dogs Depending on Their Weight. | |
| --- | --- |
| Weight (kg) | Milk product (ml/day) |
| 2-3 | 30 |
| 4-5 | 50 |
| 6-7 | 70 |

TABLE 1-continued

| Exemplary Administration Amounts for Dogs Depending on Their Weight. | |
| --- | --- |
| Weight (kg) | Milk product (ml/day) |
| 8-9 | 90 |
| ≥10 | 100 |

In another embodiment, the following amounts are administered per serving to a dog of a certain weight, preferably once a day, and preferably to a dog:

TABLE 2

| Exemplary Administration Amounts for Dogs Depending on Their Weight. | | |
| --- | --- | --- |
| Weight (Kg) | Milk product (ml/day) | Lactose administered (dependent on dose and dog weight in kg): in (g lactose)/(kg dog)/day |
| 2 | 30 | 0.5 |
| 3 | 40 | 0.5 |
| 4 | 50 | 0.4 |
| 5 | 60 | 0.4 |
| 6 | 70 | 0.4 |
| 7 | 75 | 0.4 |
| 8 | 83 | 0.4 |
| 9 | 90 | 0.4 |
| ≥10 | 100 | 0.3 |

An in vitro test of minimal inhibitory concentration (MIC) aimed to evaluate antibiotic resistances may performed for all the strains disclosed herein. The evaluated antibiotics may be the following: Gentamicin, Kanamycin, Streptomycin, Tetracycline, Erythromycin, Chloramphenicol, Clindamycin, Ampicillin, Neomycin, Penicillin, Vancomycin, Quinupristin-Dalfopristin, Linezolid, Trimethoprim, Ciprofloxacin, and Rifampicin.

The milk product of the present invention can contain further ingredients. For example, the milk product of the present invention may further comprise thickeners and/or complementary feeds/nutrients. For example, the milk product of the present invention may comprise one or more thickeners (thickening agents, namely substances which may increase the viscosity of a liquid without substantially changing its other properties, and which may improve the suspension of other ingredients or emulsions which increases the stability of the product), such as polysaccharides (pectin, vegetable gums and/or starched) or proteins. For example, the milk product of the present invention further comprises vegetable gums such as alginin, locust bean gum, xanthan gum and/or guar gum, preferably xanthan gum and/or guar gum. For example, the milk product may comprise vegetable gums such as xanthan gum and guar gum in an amount of about 0.1-0.5%, preferably about 0.3% w/v (0.3 grams of thickener (e.g., vegetable gums such as xanthan gum and guar gum) in 100 ml. The milk product of the present invention may comprise compounds that add flavor. The milk product of the present invention may comprise vitamins and/or calcium.

The present invention provides the following items:

[1] A bacterial strain deposited with the Spanish Type Cultures Collection under the deposit number CECT 9859.

[2] A fermented milk product, wherein a milk base, preferably milk, is fermented by one or several strains of bacteria isolated from a dog, optionally from dog milk or colostrum, further optionally from dog colostrum.

[3] The fermented milk product according to [2], wherein at least one strain is a lactic acid bacterium.

[4] The fermented milk product according to [3], wherein said lactic acid bacterium is from the genus *Lactobacillus*, optionally from the species *Lactobacillus reuteri*.

[5] The fermented milk product according to [3] to [4], wherein said lactic acid bacterium is the bacterial strain deposited with the Spanish Type Cultures Collection under the deposit number CECT 9859.

[6] The fermented milk product according to [2] to [5], wherein the milk is fermented by at least two strains.

[7] The fermented milk product according to [6], wherein one strain is from the genus *Streptococcus*.

[8] The fermented milk product according to [7], wherein the strain is from the species *Streptococcus thermophilus*.

[9] The fermented milk product according to [7] to [8], wherein the *Streptococcus* strain is a thermophilic strain.

[10] The fermented milk product according to [8] to [9], wherein the *Streptococcus* strain is the strain of Danisco® TA 40 LYO.

[11] The fermented milk product according to [2] to [10], wherein said fermented milk product is for the administration to a canid, optionally a canine, further optionally a dog.

[12] The fermented milk product according to [2] to [11], wherein the milk used for the production of the fermented milk product is cow milk, preferably pasteurized and/or homogenized whole cow milk.

[13] The fermented milk product according to [2] to [12], wherein said fermented milk product contains a low amount of lactose, wherein optionally a low amount of lactose means less lactose than the milk base that was used for fermentation, wherein further optionally the lactose content is 5%, preferably 10%, more preferably 15%, and even more preferably 20% less lactose than the milk base that was used for fermentation.

[14] The fermented milk product according to [2] to [13], wherein said fermented milk product does not contain added lactase and/or wherein all lactase present in the fermented milk product was produced during fermentation.

[15] The fermented milk product according to [2] to [14], wherein the milk product can be produced in a short fermentation time, preferably with less than 8 hours of fermentation, more preferably in less than 7.5 hours of fermentation, more preferably in less than 7 hours of fermentation, even more preferably in less than 6.5 hours of fermentation.

[16] The fermented milk product according to [2] to [15], wherein the fermented milk product has a pH of 4.6 or less, preferably a pH of between 4.2 and 4.6.

[17] The fermented milk product according to [2] to [16], wherein the fermented milk product contains live bacteria of the bacterial strains used for fermentation, preferably in an amount of at least $1 \times 10^8$ cfu/ml product, preferably at least $2 \times 10^8$ cfu/ml product.

[18] The fermented milk product according to [2] to [17], wherein the fermented milk product contains live bacteria of the strain deposited with the Spanish Type Cultures Collection under the deposit number CECT 9859, preferably in an amount of at least $1 \times 10^8$ cfu/ml product, preferably at least $2 \times 10^8$ cfu/ml product.

[19] A fermented milk product according to [2] to [18] or the strain of claim [1] for use as a medicament.

[20] The fermented milk product for use according to [19], wherein said medicament is for administration to a canine, preferably a dog.

[21] A fermented milk product according to [2] to [20] or the strain of claim [1] for use in treating diarrhea in a canine, preferably a dog.

[22] Use of the fermented milk product according to [2] to [18] or the strain of claim [1] in a method of improving the overall well-being, and/or improving the shininess of the coat, and/or increasing the vigor in a canid, preferably a canine, most preferably a dog.

[23] A method for producing the fermented milk product according to [2] to [22] comprising the step of fermenting a milk base, preferably milk, by one or several strains of bacteria isolated from a dog, optionally from dog milk or colostrum, further optionally from dog colostrum.

[24] The method according to [23], wherein at least one strain is a lactic acid bacterium, preferably from the genus *Lactobacillus*, more preferably from the species *Lactobacillus reuteri*.

[25] The fermented milk product according to [24], wherein said lactic acid bacterium is the bacterial strain deposited with the Spanish Type Cultures Collection under the deposit number CECT 9859.

[26] The method according to [23] to [24], further comprising packaging said fermented milk product.

EXAMPLES

Unless otherwise defined, all technical and scientific terms used herein have the same meaning as commonly understood by one of ordinary skilled in the art to which this invention belongs. Methods and materials similar or equivalent to those described herein can be used in the practice of the present invention. Additional objects, advantages and features of the invention will become apparent to those skilled in the art upon examination of the description or may be learned by practice of the invention. The following examples and drawings are provided by way of illustration, and they are not intended to be limiting of the present invention.

Example 1

Fermentation of Milk with a Reference Strain Isolated from Dog Milk

In this example, a fermented milk product was produced as a proof of concept with a *L. reuteri* reference strain (RS1) isolated from dog milk.

200 liters of cow milk were introduced into a fermentation tank heated to a temperature of 87° C. to pasteurize the milk.

After the pasteurization process, the milk was cooled to a temperature of 37° C., i.e., the incubation temperature. A starter culture of RS1 and a starter culture of a *S. thermophilus* strain was then added to the milk. The final volume of starter culture added to the cow milk was about 1% (v/v) of the total fermentation culture (1% starter culture and 99% pasteurized milk). The ratio of RS1 to *S. thermophilus* in the starter culture was 9:1 liters the present case, 1.8 liters of a starter culture of RS1 was combined with 200 ml of a starter culture of Danisco® TA 40 LYO obtained by pouring the contents of the Danisco® TA 40 LYO envelope (DuPont™) into one liter of milk. The resulting 2 liters of mixed starter culture was then added to 200 liters of milk.

Once the starter cultures are added, homogenization was carried out with the tank agitator for 5-10 minutes. Then, the culture was incubated at 37° C. until a pH of 4.6-4.5 was reached. In this case the fermentation time was 7 hours and 22 minutes to reach a final pH of 4.49.

Immediately after the end of the fermentation, the fermented product was packaged into 1 liter containers and stored at 4-8° C.

Example 2

Effect of the Fermented Milk Product on Dogs

In this example, the effect of a fermented milk product obtained according to example 1 on dogs was determined.

A strain RS1 fermented milk (from a whole UHT [ultra-high-temperature processed] commercial trade mark) was used for a first proof of concept in 37 healthy adult (>2 years) volunteer dogs.

A daily dose of 125 ml of the fermented milk was offered to fasting dogs for 7 consecutive days. Initial data of the animals was collected at the beginning of the study: Breed, age, reproductive state and diet were recorded.

Different parameters were recorded by the animal's owner. For example, on a daily basis at the offering of the product to the dogs, the voluntariness of the intake by the dog and the palatability were recorded. At the seventh day of the study, changes in the coat, the feces consistency (first, second and subsequent feces of the day), the general condition (vigor) and behavioral aspects at the offering of the product were determined.

Results

Thirty-seven dogs were recruited for this study. 34 out of 37 animals finished the trial (7 application days). The owners of three dogs decided to not to finish the study, which is common in field tests with dogs. Only data of dogs that finished the study has been further analyzed.

Breed

The product was applied to dogs of different breeds, age, reproductive state and with differing diet, as shown in the following tables. As can be seen from the tables, a large variety of different dogs was used.

TABLE 3

| Breeds Used in This Example. | |
| --- | --- |
| Breed | Number of individuals |
| English setter | 4 |
| Carea (Spanish breed) | 1 |
| Pointer | 1 |
| Mixed breed | 12 |
| German shepherd | 4 |
| Poodle | 1 |

TABLE 3-continued

| Breeds Used in This Example. | |
| --- | --- |
| Breed | Number of individuals |
| Greyhound | 1 |
| Labrador retriever | 3 |
| Bull terrier | 1 |
| West Highland White Terrier | 1 |
| Cocker Spaniel | 1 |
| Husky | 1 |
| Border Collie | 1 |
| Irish setter | 1 |
| Scottish terrier | 1 |

As can be seen, a large variety of different breeds has been used.

TABLE 4

| Age of the Dogs Used in This Example. | |
| --- | --- |
| Age (years) | number |
| <2 | 0 |
| 2-10 | 28 |
| ≥10 | 6 |

TABLE 5

| Reproductive State of the Dogs Used in This Example. | |
| --- | --- |
| Reproductive condition | number |
| Uncastrated male | 16 |
| Unsterilized female | 12 |
| Castrated male | 4 |
| Sterilized female | 2 |

TABLE 6

| Diet of the Dogs Used in This Example. | |
| --- | --- |
| Diet | number |
| Commercial feed | 13 |
| Commercial feed + food waste | 21 |

Daily Observations

The following data was obtained from daily observations of the dogs used in this study. The results of this study are shown in the tables below and in FIGS. 1 and 2.

TABLE 7

| | Day 1 | | Day 2 | | Day 3 | | Day 4 | | Day 5 | | Day 6 | | Day 7 | |
| --- | --- | --- | --- | --- | --- | --- | --- | --- | --- | --- | --- | --- | --- | --- |
| | n | % | n | % | n | % | n | % | n | % | n | % | n | % |
| Immediate intake | 27 | 79.4 | 32 | 94.1 | 33 | 97.1 | 31 | 91.2 | 30 | 88.2 | 32 | 94.1 | 32 | 94.1 |
| First explore and then eating | 6 | 17.6 | 1 | 2.9 | 0 | 0 | 1 | 2.9 | 1 | 2.9 | 0 | 0 | 0 | 0 |
| Smell and thereafter eating | 1 | 2.9 | 1 | 2.9 | 1 | 2.9 | 1 | 2.9 | 1 | 2.9 | 1 | 2.9 | 1 | 2.9 |
| Recognizing but not eating | 0 | 0 | 0 | 0 | 0 | 0 | 1 | 2.9 | 2 | 5.9 | 1 | 2.9 | 1 | 2.9 |

Evaluation of the animals' behavior at each product offer for 7 consecutive days. As can be seen, the majority of the dogs surprisingly ate the product immediately at the beginning of the study, and this number increased during the study.

TABLE 8

| Evaluation of the Product's Intake by the Dogs for 7 Consecutive Days. | | | | | | | | | | | | | | |
|---|---|---|---|---|---|---|---|---|---|---|---|---|---|
| | Day 1 | | Day 2 | | Day 3 | | Day 4 | | Day 5 | | Day 6 | | Day 7 | |
| | n | % | n | % | n | % | n | % | n | % | n | % | n | % |
| Dogs ate all the product | 32 | 94.1 | 33 | 97.1 | 33 | 97.1 | 33 | 97.1 | 33 | 97.1 | 32 | 94.1 | 33 | 97.1 |
| Started eating but did not finish the product | 1 | 2.9 | 0 | 0.0 | 0 | 0.0 | 0 | 0.0 | 0 | 0.0 | 0 | 0.0 | 0 | 0.0 |
| Tasted but did not eat | 1 | 2.9 | 1 | 2.9 | 1 | 2.9 | 0 | 0.0 | 0 | 0.0 | 0 | 0.0 | 0 | 0.0 |
| Smelled but did not taste | 0 | 0.0 | 0 | 0.0 | 0 | 0.0 | 1 | 2.9 | 1 | 2.9 | 2 | 5.9 | 1 | 2.9 |

As evident from the above data, surprisingly most dogs immediately ate all of the product at the beginning of the study, and the number of dogs that immediately ate the product surprisingly increased in the consecutive study days. This finding indicates that dogs liked the product and thus the product can be easily administered to dogs as they voluntarily eat the offered product. This easy administrability is an important and highly beneficial feature of the fermented milk product.

Evaluation at the Seventh Day of the Study

Several parameters relating, e.g., to changes in the coat of the dogs, feces, vigor and behavior were evaluated both at the beginning of the study and at the seventh day. The values obtained at the seventh day of the study were then compared to initial values.

Coat Aspect

The coat of the dogs and in particular the effect of the product on the shininess of the coat was evaluated. In general, a healthy coat should be shiny and shininess of the coat is an indicator of a dog's health. A dull coat can indicate illness, stress or a wrong diet. Thus, an increase of the coat's shininess can be an indication for an increase in health and overall wellbeing.

For each dog, it was evaluated whether the coat became more shiny, the shininess remained the same, or the coat became less shiny. The results are shown in table 3 below. As can be seen in said table, 4 dogs showed an increase in shininess, 30 dogs remained unchanged with regard to the shininess, and no dog showed a decrease in shininess. The data thus indicates that the administration of the product leads to a health benefit in at least some of the dogs. As the data was acquired after only seven days, it is to be expected that the effect increases with longer administration time.

TABLE 9

| | n | % |
|---|---|---|
| Shinier/stronger | 4 | 11.76 |
| Same | 30 | 88.24 |
| Less shiny | 0 | 0.00 |

Evaluation of the coat's aspect after the seventh administration day. As can be seen, four dogs showed an increase in shininess, while no dog showed a decrease in shininess.

Feces Evaluation

The feces of the dogs at the end of the study were compared to the feces at the beginning of the study. Comparisons were made for the first, second and third as well as further deposits resulting from the first, second and further defecations of the day. It was evaluated whether the feces consistency remained unchanged, became softer, or whether the dogs developed diarrhea.

TABLE 10

| First Deposit | | |
|---|---|---|
| | n | % |
| No changes | 28 | 82.35 |
| Softer | 6 | 17.65 |
| Diarrhea | 0 | 0.00 |

Evaluation of the feces of the first defecation of the day at the seventh administration's day compared to the start of the study.

TABLE 11

| Second Deposit (32 Evaluations) | | | |
|---|---|---|---|
| | | n | % |
| No changes | A | 29 | 90.63 |
| Softer | B | 3 | 9.38 |
| Diarrhea | C | 0 | 0.00 |

Evaluation of the feces of the second defecation of the day at the seventh administration's day compared to the start of the study.

TABLE 12

| Others (22 Evaluations) | | | |
|---|---|---|---|
| | | n | % |
| No changes | A | 19 | 86.36 |
| Softer | B | 3 | 13.64 |
| Diarrhea | C | 0 | 0.00 |

Evaluation of the feces of the third or further defecations of the day at the seventh administration's day compared to the start of the study.

General Condition—Vigor

Dogs were evaluated with regard to their vigor, in particular when going for a walk and during activities at home or in the garden. The dog's vigor at the seventh day was compared to that at the start of the study. As can be seen in table 6, thirty dogs showed no difference with regard to the vigor, while four dogs showed better vigor at the seventh day of the study. No dog showed a decrease in vigor after the study. This demonstrates that surprisingly, the product when administered to dogs can lead to an improvement of the dog's vitality.

TABLE 13

Evaluation of the General Condition/Vigor
at the Seventh Administration's Day

|  |  | n | % |
| --- | --- | --- | --- |
| Better | A | 4 | 11.76 |
| Same | B | 30 | 88.24 |
| Worse | C | 0 | 0.00 |

Behavior at the Product Offer Dogs were evaluated with regard to how they react to offered product at the seventh study day. Most dogs immediately ate the offered product. These results further demonstrate that surprisingly, dogs in general like the product and the product can thus easily be administered orally.

Example 3

Identification of Further Strains from Dog Colostrum

The aim of this example was to isolate further strains with possibly improved properties. To this end, the colostrum of three different Spanish Mastiff bitches was harvested. For isolation of strains, 100 μl of colostrum milk were seeded on an MRS (Manosa, Rogosa and Sharpe, Oxoid) agar plate, in triplicate per sample. The plates were incubated in an anaerobiosis oven for 24 hours at 41° C. Colonies with different morphology were inspected microscopically after Gram staining. Gram positive colonies were tested for the presence of catalase, and those negative for catalase were seeded on MRS plates. The plates were incubated 24 hours at 37° C. Once a pure culture was obtained, grown bacteria were collected from the MRS medium and preserved in freezing cryovials with skim milk that were stored at –80° C. The Gram-positive and catalase-negative colonies were treated as presumed lactic acid bacteria. In total, 43 isolates were obtained by the above described method.

Example 4

Characterization of the Strains Isolated in Example 3

In this example, the strains isolated in example 3 were further analyzed with regard to, e.g., species, antibiotic resistance, and antimicrobial activity.

Example 4.1

Identification of the Species of the Isolated Strains

In order to determine the species of the strains isolated in example 3, parts of their genome were sequenced. To this end, DNA was isolated from each culture and a region of interest (the rDNA 16S gene) was amplified. Subsequently, the amplicon was purified and sequenced in both directions.

Once the sequences were obtained, the contig of both sequences was constructed. For the identification of bacteria, the sequences were entered into databases such as the Genbank NCBI (National Center for Biotechnology Information, http://www.ncbi.nlm.nih.gov) with the BLAST program (http://www.ncbi.nlm.nih.gov/BLAST) by comparison with sequences of known species, the species of the isolated cultures could be identified. The results are shown in FIG. 3. As can be seen from the figure, of the 42 presumed lactic acid bacteria, 13 strains were *Lactobacillus animalis*, 10 strains were *Lactobacillus reuteri*, 9 strains were *Enterococcus faecalis*, 4 strains were *Lactobacillus johnsonii*, 3 strains were *Lactobacillus plantarum*, 1 strain was *Enterococcus avium*, 1 strain was *Enterococcus faecium*, and 1 isolate was a mixed culture of different strains.

Example 4.2

Antibiotic Resistance of Identified Strains

It was evaluated whether the strains show resistance to antibiotics. The antibiotic resistance of the strains was evaluated using the VetMic system. VetMIC is a system based on the MIC (minimum inhibitory concentration). The MIC corresponds to the lowest concentration of antibiotic (expressed in μg/ml) that is able to inhibit bacterial growth. The strains were tested with the following antibiotics: Gentamicin, Kanamycin, Streptomycin, Erythromycin, Clindamycin, Tetracycline, Chloramphenicol, Neomycin, Ampicillin, Penicillin, Vancomycin, Quinupristin-Dalfopristin, Ciprofloxin, Trimethoprim, Linezolid and Rifampicin. The MICs of each strain and antibiotic were then compared with the values that EFSA requires for strains used in animal feed (EFSA. 2018. Guidance on the characterization of microorganisms used as feed additives or as production organisms. EFSA Journal, 16(3):5206).

Experimental Setup

20 μl of each strain conserved at –80° C. were seeded on an MRS agar plate under a laminar flow hood. Each culture was incubated in the anaerobiosis oven on the MRS plate for 24 hours at 37° C. Isolated colonies of the different strains were taken and resuspended in a glass jar with 5 ml of sterile saline solution, until reaching a turbidity of 1 on the McFarland scale ($3\times0.10^8$ cfu/ml). The saline solution was diluted 1:1000 in LSM broth (90% IST broth (IsoSensitest broth) and 10% MRS broth), reaching a turbidity of $3\times10^5$ cfu/ml. In the negative control wells of the microplates, 200 μl of LSM broth was added. In the positive control wells of the microplates, 100 μl of LSM broth and 100 μl of the inoculum preparation were added, remaining at a concentration of $3\times104$ cfu/well. In the wells with antibiotics, 100 μl of LSM broth and 100 μl of the inoculum preparation were added, remaining at a concentration of $3\times10^4$ cfu/well. The microplates were then incubated in anaerobic conditions at 37° C. for 48 hours.

The results obtained are shown in FIG. 4. As can be seen from said figure, several strains perform better than strain RS1. For example, strain CECT 9859, which is also a *L. reuteri* strain, meets the MIC requirements of the EFSA with regard to most antibiotics, including Tetracycline. This is in particular noteworthy as, e.g., strain RS1 does not meet the EFSA requirements with regard to lack of Tetracycline resistance. These further strains are beneficial for the administration to animals, including dogs. In particular, strain CECT 9859 was chosen as a promising candidate for a fermented milk product that is an improvement over the fermented milk product described in example 1.

Example 4.3

Comparison Between Aquilon *L. reuteri* Isolates According to Antimicrobial Activity on Pathogenic *E. coli* Strains In this example, two strains identified in the present invention, strain 3.3 and strain CECT 9859, were compared to strain RS1 with regard to the antimicrobial activity. It was found that strain CECT 9859 was by far the best performing strain.

In order to determine the antimicrobial activity of the isolated lactic acid bacteria (BAL) a spot test was performed, more particularly a modification of the protocol described by Schillinger & Lücke, 1989. Appl Environ Microbiol. 55(8): 1901-1906, confronting the isolated BAL with isolated pathogenic *Escherichia coli* which were isolated in the Department of Animal Health Group Digesporc (ULE) from clinical cases and dogs from the veterinary hospital of the ULE. All tests were performed in triplicate.

Results

The results are shown in table 14. All the strains of *L. reuteri* confronted with the six strains of *E. coli* showed inhibition halos. Strain CECT 9859 showed the best results as it scored best against 4 of the 6 pathogenic strains analyzed, in particular against the strains less resistant to antibiotics. These strains are believed to initiate the infection in natural conditions in antibiotic restrained dogs, as these dogs are commonly infected by such strains. Increased inhibition of these strains is thus highly beneficial and strain CECT 9859 is expected to deliver better protection against these initial infectious strains. It is worth noting that the acquisition of antibiotic resistance genes is advantageous for bacteria living in environments with antibiotics. However, such genes may provide an evolutionary disadvantage in environments where antibiotics are absent (Basra et al., 2018. *Genom Biol Evol.* 10(2): 667-669; Melnyk et al., 2015. *Evol Appl.* 8(3): 273-283). Dog feeds does not contain antibiotics and dogs are generally not treated with antibiotics, unless necessary. Thus, without being bound by a particular theory, in a real world setting it is more likely that the relevant *E. coli* strains will have a low resistance to antibiotics.

TABLE 14

| | *E. coli* strains | | | | | |
| | High resistance against antibiotics | | | Low resistance against antibiotics | | |
| | 2/16 | 25/15 | 97/17 | 49/18A | 5/19 | 31/18 |
| *L. reuteri* CECT 9859 | 21 mm | 21 mm | 18 mm | 24 mm | 25.6 mm | 24 mm |
| *L. reuteri* 3.3 | 21 mm | 24 mm | 20 mm | 24 mm | 24.6 mm | 21 mm |
| *L. reuteri* RS1 | 18 mm | 21.3 mm | 23 mm | 20 mm | 25 mm | 18 mm |

Preparation of Lactic Acid Bacteria Spot Plates

The lactic acid bacteria isolates were seeded in 5 ml MRS broth and cultured for 18 to 24 hours at 39° C. under anaerobic conditions. Thereafter, six times 10 µl of the culture were put on a MRS agar plate tempered at 37° C., the so-called spots. The plates were then incubated for 24 hours at 39° C. under anaerobic conditions.

Preparation of Pathogenic Bacteria

Six *E. coli* strains of canine origin were used to test antimicrobial activity against: *E. coli* 2/16, *E. coli* 25/15, *E. coli* 97/17, *E. coli* 49/18A, *E. coli* 5/19 and *E. coli* 31/18. The first three strains had the highest resistance to antibiotics with which they were confronted and the last three had the highest sensitivity to these.

The pathogenic *E. coli* strains were seeded on TSA (tryptone soy agar) plates and incubated for 24 hours at 37° C. under aerobic conditions. Thereafter, the *E. coli* strains were seeded into 5 ml BHI broth and incubated for 24 hours at 37° C. under aerobic conditions. Thereafter, a semisolid BHI agar was prepared from a BHI broth supplemented with 0.7% bacteriological agar. The BHI agar was heated to 44° C. and inoculated with 1% of the *E. coli* culture.

Spot Assay 10-15 ml of the inoculated BHI agar was used to evenly coat the MRS agar plates with lactic acid bacteria spots from paragraph [0116]. The agar was allowed to solidify, and the plates were subsequently cultured for 24 hours at 37° C. under aerobic conditions. After 24 hours, the diameter of the inhibition zones visible as halos around the spots of the lactic acid bacteria were measured. These are indicative of inhibition the growth of the pathogenic *E. coli* bacteria.

Size (in mm) of the inhibition halos generated by the spots of the BAL strains against the strains of *E. coli.*

Example 4.4

Further Evaluation of Antimicrobial Activity of CECT 9859

In order to further determine the antimicrobial activity of CECT 9859, further spot tests as described in example 4.3 above were performed. To this end, CECT 9859 was tested against four pathogens, each represented by 6 different strains, that affect canids: *Salmonella enterica* subsp. *enterica* serovar *typhimurium* (in the following *Salmonella typhimurium* or *S. typhimurium*) (strains: 51, S4, S6, S7, S10 and S11), *Escherichia coli* (strains: 2/16; 5/19; 25/15; 31/18; 49/18A and 97/17), *Clostridium perfringens* (Type A: Cp1; Cp8; Cp19; Cp21; Cp57 and Cp58) and *Clostridium difficile* (strains: Cd1; Cd2; Cd3; Cd4; Cd5 and Cd6). The pathogenic strains were selected for this test according to the number of antibiotics those strains are resistant to and their level of antibiotic resistance, so that those that show the highest and the lowest resistance to different antibiotics were chosen. The strains of *Salmonella thyphimurium* and *Escherichia coli* are canid isolates, while the isolates of *Clostridium* sp. are of pig origin. All tests were done in triplicate.

Preparation of CECT 9859 Spot Plates

Preparation of CECT 9859 spot plates was performed according to the protocol described in example 4.3 adapted to culturing conditions of the respective pathogens: *S. thyphimurium* and *E. coli* were seeded on TSA agar (Tryptone Soy agar, Oxoid) under aerobic conditions at 37° C., for 24 hours. *C. perfringens* and *C. difficile* were seeded on FAA (Fastidius Anaerobe agar, Oxoid) under anaerobic conditions at 39° C., for 24 hours. The pathogenic microorganisms were then inoculated into 5 ml of BHI broth (Brain Heart Infusion broth, Oxoid) and incubated under their optimal growth conditions, specified above. The spot assay in the MRS plates was performed under the conditions described above for the pathogenic microorganisms. After 24 hours of incubation, the measurement of the inhibition halos generated around the spots in the growth of the pathogen was carried out.

Results

The results are shown in table 16 below. The mean of the inhibition halos of *Lactobacillus reuteri* CECT 9859 against the different pathogens was 22.93 mm in diameter.

This inhibitory activity is significant. According to Schillinger & Lücke (Schillinger, U. & Lücke, F. K. 1989. Antibacterial activity of *Lactobacillus* sake isolated from meat. Appl. Environ. Microbiol. 55(8): 1901-1906), inhibitions superior to 11 mm are indicative of antimicrobial activity. The fact that the inhibition acts both on antibody resistant and antibody sensitive bacteria is a strong element in favor of the use of this strain to treat dysbiosis (an imbalance in the number or type of microbial colonies that have colonized an animal) and/or as a complementary treatment together with agents known to cause dysbiosis.

Inhibition zones for strains of (A) *Salmonella typhimurium*, (B) *C. perfringens* type A, (C) *Escherichia coli*, and (D) *C. difficile*.

Example 4.5

Characterization of pH Decreasing Activity

In order to characterize the pH decreasing activity of *Lactobacillus reuteri* CECT 9859, an important attribute to establish its capability to prevail in complex microbiological communities, the strain was seeded in MRS broth and incubated at 18 hours under anaerobic conditions and 38° C., following the method described in Schillinger & Lücke (1989). 1 ml of the bacterial suspension was then inoculated in 9 ml of MRS broth with a pH of 6.5, incubating in the same conditions described above, but under agitation (100 rpm). After 48 hours of incubation, the pH of the medium was determined. The test was carried out in triplicate. It is considering that an isolate has the capacity to lower the pH of the medium when it reached values below 4.5.

Results

A pH of 4.24±0.00 was measured.

Conclusions

*Lactobacillus reuteri* CECT 9859 is able to reduce the pH of the media below the 4.5 threshold, an attribute considered significant and indicative of probiotic activity.

Example 4.6

Characterization of Tolerance to Bile Salts

Tolerance or preference for growth in bile salts is a key parameter for establishing probiotic potential. To measure

TABLE 16

| *Salmonella Typhimurium* | | | | | |
|---|---|---|---|---|---|
| High resistance to antibiotics | | | Low resistance to antibiotics | | |
| (A) | | | | | |
| S4 | S6 | S7 | S1 | S10 | S11 |
| *Lactobacillus reuteri* CECT 9859 | | | | | |
| 23.3 ± 3.1 | 21.0 ± 3.0 | 16.7 ± 5.0 | 21.7 ± 5.5 | 26.0 ± 3.6 | 24.0 ± 3.5 |

| *C. perfringens* type A | | | | | |
|---|---|---|---|---|---|
| High resistance to antibiotics | | | Low resistance to antibiotics | | |
| (B) | | | | | |
| Cp8 | Cp21 | Cp57 | Cp1 | Cp19 | Cp58 |
| *Lactobacillus reuteri* CECT 9859 | | | | | |
| 15.3 ± 3.1 | 22.0 ± 3.5 | 19.7 ± 4.5 | 21.0 ± 3.6 | 21.3 ± 3.1 | 18.3 ± 3.5 |

| *Escherichia coli* | | | | | |
|---|---|---|---|---|---|
| High resistance to antibiotics | | | Low resistance to antibiotics | | |
| (C) | | | | | |
| 2/16 | 25/15 | 97/17 | 49/18A | 5/19 | 31/18 |
| *Lactobacillus reuteri* CECT 9859 | | | | | |
| 21.0 ± 3.0 | 21.0 ± 1.0 | 24.0 ± 1.7 | 24.0 ± 1.0 | 25.6 ± 0.4 | 24.0 ± 2.0 |

| *C. difficile* | | | | | |
|---|---|---|---|---|---|
| High resistance to antibiotics | | | Low resistance to antibiotics | | |
| (D) | | | | | |
| Cd 2 | Cd 3 | Cd 5 | Cd 1 | Cd 4 | Cd6 |
| *Lactobacillus reuteri* CECT 9859 | | | | | |
| 23.3 ± 4.2 | 28.0 ± 3.5 | 23.3 ± 1.2 | 26.3 ± 0.6 | 25.3 ± 2.3 | 20.7 ± 1.2 |

27 this, the protocol described by Monteagudo Mera (Monteagudo Mera, A. 2011. Selección in vitro de microorganismos con potencial probiótico. Tesis doctotal. Universidad de León) was followed with slight modifications. *Lactobacillus reuteri* CECT 9859 was grown in MRS broth at pH 6.2 incubating for 18-24 hours until reaching an approximate concentration of $10^9$ cfu/ml. After this incubation period, 1 ml of the culture was used to inoculate three tubes: a control with MRS broth at pH 6.2, a tube with MRS broth at pH 8.0 (adjusted using 1 N NaOH, Sigma-Aldrich) and supplemented with 0.45% bile salts (Cultimed) and a tube with MRS broth at pH 8.0 supplemented with 0.35% bile salts. These tubes were incubated at 37° C. under anaerobic conditions for 4 hours and shaking (100 rpm).

Once the incubation was completed, viable colonies were counted at different times: 0, 2 and 4 hours (h0, h2 and h4, respectively). For this, decimal dilutions were made in microtubes with 900 µl of peptone water and 100 µl of the last four dilutions were seeded ($10^{-5}$ to $10^{-8}$ in the control group and $10^{-3}$ to $10^{-6}$ in the groups with bile salts) on MRS agar plates. After a 48-hour incubation under anaerobic conditions, the cfu count was determined. Percentage of growth is measured against that at time zero at pH 6.2.

Results

TABLE 17

| | 0.45% bile salt | | 0.35% bile salt | |
|---|---|---|---|---|
| | h2 | h4 | h2 | h4 |
| *Lactobacillus reuteri* CECT 9859 | 23.33% | 24.44% | 311.11% | 170% | cfu after incubation in the presence of bile salts. The values are relative to that of the control at the same time point.

Conclusions

The percentage of viable bacteria in the presence of 0.45% of bile salts was 23.33 and 24.44 at two and four hours. In the case of incubation with 0.35% bile salts, the values were very different compared to incubation with 0.45% bile salts. The values in this case showed a significant increase compared to the controls at 2 and 4 hours, indicating that the incubation of *Lactobacillus reuteri* CECT 9859 with this concentration of bile salts stimulates its growth.

Example 4.7

Further Characterization of Antibiotic Resistance of CECT 9859

In this example, the antibiotic susceptibility of *Lactobacillus reuteri* CECT 9859 to different antibiotics was determined by broth microdilution with two different culture broths, as indicated in the EFSA FeedAp Opinion (The EFSA Journal, 2018). Experiments were done following the indications of the Clinical and Laboratory Standard Institute—CLSI—(formerly National Committee for Clinical Laboratory Standards—NCCLS). The following antibiotics were tested: ampicillin, gentamicin, streptomycin, kanamycin, tetracycline, chloramphenicol, clindamycin, vancomycin, and erythromycin. Since the methodology in this example differs from that of example 4.2, the results can differ between these two examples.

Material and Methods

General microbiological and laboratory techniques were similar to those described in standard text books (Madigan et al. 2003. Brock Biology of Microorganisms (10th ed.) Prentice Hall) (Prescott et al. 2002. Microbiology. 5th Edition. McGraw-Hill Inc. New York). Water of high quality obtained using the Milli-RX 20 and the Milli-Q Plus 185 apparatus (Millipore) was used in this experiment. DeMan Rogosa Sharpe Broth and Agar (MRS and MRS agar, Oxoid Laboratories) and Mueller-Hinton (Oxoid Laboratories) were prepared and used in accordance with the manufacturer's instructions, using Milli-Q water. LAB susceptibility test medium (LSM) consists of a mixture of IST (Oxoid laboratories) broth (90%) and MRS broth (10%) adjusted to pH 6.7, as previously described (Klare et al. 2005. Evaluation of new broth media for microdilution antibiotic susceptibility testing of Lactobacilli, Pediococci, Lactococci, and Bifidobacteria. Applied and Environmental of Microbiology, 71: 8982-8986.). Media for these studies were incubated in air-tight jars. To create anaerobic atmosphere, the BBL™ GasPak™ Plus Anaerobic System envelopes with palladium catalyst (BD Laboratories) was used. An appropriate GasPak™ indicator was added in each jar to assure that desired conditions were obtained. Cultures were incubated overnight for 24 hours, unless otherwise stated. Unless otherwise stated, cultures were incubated at 37° C. Standard plating was performed using culture spreading with a sterile disposable inoculating loop holder kolle and plates were examined visually. Incubation of cultures was performed in a Rotabit (Selecta). Centrifugation was performed in an Eppendorf apparatus. Water bath was from Selecta. The stock solutions (1.048 mg ml-1) of the antibiotics ampicillin, gentamicin, streptomycin, kanamycin, clindamycin, vancomycin and tetracycline were prepared by dissolving with Milli-Q sterile water and filtering through a membrane filter of 0.45 µm (Millipore). Chloramphenicol and erythromycin stock solution was prepared similarly except that ethanol was the solvent used. Stock solutions were stored at −20° C. until their use.

A culture of CECT 9859 was grown in an anaerobic atmosphere in MRS broth or agar (Oxoid Laboratories) at 37° C. overnight (18 hours) and used for the antibiotic susceptibility study in order to assess the minimum inhibitory concentration (MIC) for erythromycin and the other antibiotics described in the EFSA 2018 guidelines (EFSA FEEDAP Panel (EFSA Panel on Additives and Products or Substances used in Animal Feed), Rychen et al., 2018. Guidance on the characterization of microorganisms used as feed additives or as production organisms. EFSA Journal 2018; 16 (3): 5206, 24 pp. https://doi.org/10.2903/j.efsa.2018.5206.). *S. aureus* ATCC25923 was used as a control strain. For this purpose, broth microdilution methodology using MRS medium and LSM medium was applied. The technique was made following indications of the Clinical and Laboratory Standard Institute—CLSI—(formerly National Committee for Clinical Laboratory Standards—NCCLS) (CLSI. Performance Standards for Antimicrobial Susceptibility Testing. 27th ed. CLSI supplement M100). The MIC determination for *Lactobacillus reuteri* CECT 9859 strain was done under anaerobic atmosphere conditions at 37° C. for 24 h.

Interpretation Criteria

According to the CLSI definition, the MIC is considered the lowest concentration of an antimicrobial agent that prevents visible growth of a microorganism in the broth dilution susceptibility test. The categorization of the microorganisms as susceptible or resistant to the antimicrobial tested was made according to the definitions included in the EFSA 2018 Opinion (EFSA, 2008. Update of the criteria used in the assessment of bacterial resistance to antibiotics of human or veterinary importance. The EFSA Journal, 732: 1-15.).

Results

The MIC for ampicillin, streptomycin, gentamicin, kanamycin, tetracycline, chloramphenicol clindamycin, vancomycin, and erythromycin antibiotics were studied against *Lactobacillus reuteri* CECT 9859 strain, using the broth microdilution methodology with MRS medium and LSM media. Two culture media were used since differences in MICs had been reported by EFSA (2008) related to possible interference of the growth media. The results obtained for *Lactobacillus reuteri* CECT 9859 strain are shown in Table 18. Those obtained for *S. aureus* ATCC25923 strain are shown in Table 19.

TABLE 18

| Antibiotic | EFSA (2018) values | *Lactobacillus reuteri* CECT 9859 | | | |
|---|---|---|---|---|---|
| | | MRS | Category | LSM | Category |
| Ampicillin | 2 | 0.25 | S | 0.25 | S |
| Gentamicin** | 8 | 16 | R | 2 | S |
| Streptomycin** | 64 | 128 | R | 16 | S |
| Kanamycin** | 64 | 512 | R | 64 | S |
| Tetracycline | 32 | 4 | S | 8 | S |
| Chloramphenicol | 4 | 4 | S | 4 | S |
| Vancomycin | nr | >512 | R | 512 | R |
| Clindamycin | 4 | 0.25 | S | 0.25 | S |
| Erythromycin | 1 | 0.25 | S | 0.125 | S |

**EFSA (2008) indicated possible interference of the growth medium.
S, susceptible;
R, resistant;
nr, not required Microbiological breakpoints categorizing bacteria as resistant (mg L-1) (EFSA, 2018). Strains with MICs higher than the breakpoints are considered as resistant.

TABLE 19

| Antibiotic | CLSI values | MH | Category |
|---|---|---|---|
| Ampicillin | ≤0.25 | 0.125 | S |
| Gentamicin | ≤4 | 0.125 | S |
| Streptomycin | nd | 2 | |
| Kanamycin | ≤6 | 2 | S |
| Tetracycline | ≤4 | 1 | S |
| Chloramphenicol | ≤8 | 4 | S |
| Vancomycin | ≤2 | 1 | S |
| Clindamycin | ≤0.5 | 0.125 | S |
| Erythromycin | ≥8 | 0.125 | S |

Microbiological cut-off values (mg L-1) in the *S. aureus* strain. S, susceptible; R, resistant; nd, no data.

These results were reproducible and were further confirmed in duplicate experiments. Differences were observed in MIC values for some antibiotics when MRS or LSM medium was used. Among lactic acid bacteria, the interference of the growth medium further complicates the susceptibility testing as reported in EFSA Journal (2008). Specific media have been described to alleviate this problem (Klare et al., 2005).

The data suggest that *Lactobacillus reuteri* CECT 9859 strain is resistant to vancomycin. Resistance to vancomycin is typical of heterofermentative lactobacilli such as *L. reuteri* and is related to constitutive presence of a modified precursor of the cell wall peptidoglycan. This form of resistance is not transferable and not a cause for concern, according to EFSA (EFSA, 2005. Opinion of the Scientific Panel on Additives and Products or Substances used in Animal Feed on a request from the Commission on micro-organism product "*Reuteri* Pig Powder" for use as feed additive in accordance with Council Directive 70/524/EEC. The EFSA Journal, 229: 1-7).

MIC value obtained with LSM medium for kanamycin and chloramphenicol in *Lactobacillus reuteri* CECT 9859 strain is similar to the breakpoint specified by EFSA. Moreover, it is necessary to emphasize that with respect kanamycin, gentamicin and streptomycin important discrepancies were observed when using MRS or LSM broth. EFSA (2008) considers that these differences may be related to interference of the growth medium.

Example 5

Preparation of a Fermented Milk Product with Strain CECT 9859

In this example, a fermented milk product was produced with strain CECT 9859 according to the following protocol.

Seeding Plates

20 µl of each strain of *L. reuteri* conserved at −80° C. was sown on a MRS plate in laminar flow cabin. The plates were incubated 24 hours at 37° C. in an anaerobic incubator.

Preparation of the Starter Culture

For each strain, a single colony of the above prepared plate was taken with a sowing loop and introduced into a centrifuge tube containing 4 ml of MRS liquid Medium. The culture was incubated for 24 hours in an incubator at 37° C. Subsequently, the culture was centrifuged at 4400 rpm for 15 minutes. The supernatant was removed, and the precipitate was resuspended into 4 ml of 0.9% sterile saline solution. Serial dilutions of the resuspension were made with 1 ml diluted in 9 ml of saline solution per dilution step and compared to the McFarland standard until a turbidity equal to the McFarland standard 0.5 was reached, corresponding to a cell density of $1-2 \times 10^{-8}$ CFU/ml.

Preparation of a Fermentation Adjuvant from Danisco® TA 40 LYO 100 DCU

Danisco® TA 40 LYO is a thermophilic culture of *Streptococcus thermophilus* that can be used in the production of yogurt and sour milk. It was used to prepare a fermentation adjuvant for the production of the fermented milk product. One envelope of Danisco® TA 40 LYO (DuPont™) 100 DCU (Danisco culture units), containing *Streptococcus thermophilus* was poured into one liter of pasteurized and homogenized whole cow's milk.

Production of a Fermented Milk Product With Strains of Canine Origin

For each strain, two cultures of 250 ml were produced as duplicates. For each culture, an appropriate amount of cow's milk was inoculated with 0.9% of the starter culture of paragraph [0145], and 0.1% of the fermentation adjuvant of paragraph [0146]. The cultures were incubated at 37° C. until the desired clot density was reached. The product had a good overall appearance. Different phases were not observed.

Determination of pH and Titratable Acidity of the Fermented Milk Product

The pH and the titratable acidity of the fermented milk products obtained in step D above were determined. The pH was determined with a pH electrode. The titratable acidity was determined by titration with a solution of 0.1 N NaOH and phenolphthalein as an indicator according to the standard FIL-IDF 150 (1991).

After a fermentation time of 7 hours and 18 minutes (first fermentation experiment of the duplicates) and 6 hours and 55 minutes (second fermentation experiment of the duplicates), i.e., in average after about 7 hours and 10 minutes, a pH of 4.6 (the isoelectric point of casein) was reached. This fermentation time is considerably smaller than that of RS1, which reached a pH of 4.6 after 8 hours in an equivalent experiment in which the same procedure and parameters were used. It is believed that a further reduction in fermentation time will occur when fermenting at a larger scale, similar to effects observed when moving from small-scale to industrial scale fermentation with strain RS1. It is expected that in industrial scale production, the cultivation time will be about 1 hour shorter than that of RS1 in an equivalent setup.

Example 6

Administration of CECT 9859 Fermented Milk Product to Dogs with Bad Intestinal Health In this example, CECT 9859 fermented milk product ("Yogdog") was administered to dogs with bad intestinal health in order to evaluate the general acceptance of the product, the overall impression on the owners, the impact on stool quality, the impact on animal behavior, and the impact on animal appearance. For example, 5 of the tested dogs had dysbiosis of different origin. Owners were offered to participate in the study by their veterinaries following clinical criteria (animals with conditions making them prone to present diarrhea or ingestion disorders).

Administration

Animals were administered weight-adjusted amounts of the fermented milk product once a day from day 1 to day 10 of the study, between normal feeding hours (i.e., if the animals use to eat in the morning and in the evening, the product was administered at noon). The amounts were chosen to avoid administration of more than 1 g lactose/kg dog. For a dog of 4 kg or below, 20 ml of fermented milk product (less than 0.1825 g lactose/kg dog) were administered. For a dog between 5 and 8 kg, 25 ml of fermented milk product (0.18-0.11 g lactose/kg dog) were administered. For a dog between 9 and 15 kg, 35 ml of fermented milk product (0.14-0.09 g lactose/kg dog) were administered. For a dog between 16 and 30 kg, 45 ml of fermented milk product (0.10-0.05 g lactose/kg dog) were administered. For a dog above 30 kg, 50 ml of fermented milk product (less than 0.06 g lactose/kg dog) were administered.

Study Animals

A total of 17 dogs participated in the study (see table in FIG. 5).

Data collection from day 1 to 10

Owners were given a data collection form in which they were asked to register the following observations:

Voluntary intake:

Score "a" if the dog smells and eats immediately

Score "b" if the dog smells and eats later

Score "c" if the dog doesn't eat the product

A change over the course of the study from "c" to "b" or "b" to "a" or "c" to "a" was considered and improvement.

Palatability:

Score "a" if the dog eats all the product

Score "b" if the dog eats some of the product

Score "c" if the dog smells the product but doesn't taste it

A change over the course of the study from "c" to "b" or "b" to "a" or "c" to "a" was considered and improvement.

Stool quality:

Owners were given a scale from 1 to 7 with photographic support and description, being 1 the hardest and 7 the loosest stool. Scores 2, 3 and 4 are considered normal. Moving from extreme values towards ideal values 2, 3 or 4 is considered improvement.

Data collection after 15 days

Owners were asked to evaluate the following points:

Quality of hair:

Score "a" if the hair appears to be less brilliant or weaker (less structural strength, brittle or rough hair)

Score "b" if there is no noticeable change in hair quality ("same")

Score "c" if the hair appears to be more shiny or stronger

"a" was considered worse hair, "c" was considered improved hair.

General attitude—vigor, in particular when going for a walk and during activities at home or in the garden:

Score "a" if the general attitude was worse

Score "b" if the general attitude didn't change ("same")

Score "c" if the general attitude of the dog was better

Attitude towards the product:

Score "a" if the dog tended to avoid the product

Score "b" if the dog was indifferent to the product

Score "c" if the dog was enthusiastic about the product

Results 7 dogs completed the study, 1 dog completed the first 9 days, 2 dogs completed the first 7 days and 5 dogs completed the first 5 days. For evaluating the results, the last observation for each dog was used.

TABLE 20

| Results for Consumption and Stool Quality | | | | |
|---|---|---|---|---|
| | | Voluntary intake | Palatability | Stool Quality |
| Day 5 | Worse | 0% | 6% | 6% |
| | Same | 82% | 94% | 70% |
| | Better | 18% | 0% | 24% |
| Day 10 | Worse | 0% | 6% | 6% |
| | Same | 82% | 94% | 76% |
| | Better | 18% | 0% | 18% |

TABLE 21

| Results for Hair Quality and General Attitude | | |
|---|---|---|
| | Quality of hair | General attitude |
| Worse | 0% | 0% |
| Same | 88% | 94% |
| Better | 12% | 6% |

As a result, it was found that the product was accepted very well by the dogs, with 94% eating the product while one dog was indifferent to the product. The product was in general well tolerated and it was found that administration led to an improvement of stool quality. It was furthermore found that the dogs liked the product even if not hungry or after repeated consumption. Also, overall aspects of the dogs (hair and general attitude) showed an improvement.

All patents, patent applications and publications referred to in the present invention are hereby incorporated by reference in their entirety.

The various embodiments described above can be combined to provide further embodiments. All of the U.S. patents, U.S. patent application publications, U.S. patent applications, foreign patents, foreign patent applications and non-patent publications referred to in this specification and/ or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A starter culture comprising a bacterial isolate suitable for producing a fermented milk product, comprising an effective amount of a bacterial strain deposited with the Spanish Type Cultures Collection under the deposit number CECT 9859, wherein the effective amount of the bacterial strain is from $1\times10^8$ to $2\times10^8$ cfu/ml of the starter culture.

2. A fermented milk product, wherein a milk base is fermented by one or several strains, wherein one of these strains is the bacterial strain deposited with the Spanish Type Cultures Collection under the deposit number CECT 9859.

3. The fermented milk product according to claim 2, wherein the milk base is fermented by at least two strains, wherein one strain is from the species *Streptococcus thermophilus*.

4. The fermented milk product according to claim 2, wherein the milk base is fermented only by the bacterial strain deposited with the Spanish Type Cultures Collection under the deposit number CECT 9859.

5. The fermented milk product according to claim 2, wherein said fermented milk product is for the administration to a canid.

6. The fermented milk product according to claim 2, wherein the milk base used for the production of the fermented milk product is cow milk.

7. The fermented milk product according to claim 2, wherein the milk product can be produced in a short fermentation time.

8. The fermented milk product according to claim 2, wherein the fermented milk product has a pH of 4.6 or less.

9. The fermented milk product according to claim 2, wherein the fermented milk product contains live bacteria of the bacterial strains used for fermentation.

10. A method of improving the overall well-being, and/or improving the shininess of the coat, and/or increasing the vigour in a canid, comprising administering the fermented milk product according to claim 2 to the canid.

11. A method for producing the fermented milk product of claim 2, comprising the step of fermenting a milk base with one or several strains of bacteria, wherein one of these strains is the bacterial strain deposited with the Spanish Type Cultures Collection under the deposit number CECT 9859.

12. The method according to claim 11, wherein the milk base is fermented only by the bacterial strain deposited with the Spanish Type Cultures Collection under the deposit number CECT 9859.

13. The method according to claim 11, further comprising packaging said fermented milk product.

14. A method of preventing and/or treating dysbiosis and/or diarrhoea in an animal in need thereof, comprising administering a fermented milk product according to claim 2 to the animal.

15. The fermented milk product according to claim 2, wherein the milk base is milk.

16. The fermented milk product according to claim 5, wherein said canid is a dog.

17. The fermented milk product according to claim 6, wherein the milk used for the production of the fermented milk product is pasteurized and/or homogenized whole cow milk.

18. The fermented milk product according to claim 7, wherein the fermentation time is less than 8 hours.

19. The fermented milk product according to claim 9, wherein the fermented milk product contains the live bacteria in an amount of at least $1\times10^8$ cfu/ml product.

* * * * *